US010562021B2

(12) United States Patent
Nowak et al.

(10) Patent No.: US 10,562,021 B2
(45) Date of Patent: Feb. 18, 2020

(54) DISPENSER FOR AN ANALYZER

(71) Applicant: Beckman Coulter, Inc., Brea, CA (US)

(72) Inventors: Kevin L. Nowak, Minnetonka, MN (US); Troy M. Coolidge, Victoria, MN (US); Glenn A. Davis, Minnetonka, MN (US)

(73) Assignee: Beckman Coulter, Inc., Brea, CA (US)

( * ) Notice: Subject to any disclaimer, the term of this patent is extended or adjusted under 35 U.S.C. 154(b) by 146 days.

(21) Appl. No.: 15/563,942

(22) PCT Filed: Mar. 18, 2016

(86) PCT No.: PCT/US2016/023255
§ 371 (c)(1),
(2) Date: Oct. 2, 2017

(87) PCT Pub. No.: WO2016/149666
PCT Pub. Date: Sep. 22, 2016

(65) Prior Publication Data
US 2018/0126372 A1     May 10, 2018

Related U.S. Application Data

(60) Provisional application No. 62/135,580, filed on Mar. 19, 2015.

(51) Int. Cl.
*B01L 3/02* (2006.01)
*G01N 35/00* (2006.01)
*G01N 35/10* (2006.01)

(52) U.S. Cl.
CPC ..... *B01L 3/0293* (2013.01); *B01L 2300/1827* (2013.01); *B01L 2300/1888* (2013.01);
(Continued)

(58) Field of Classification Search
CPC ............................................. G01N 2035/00425
See application file for complete search history.

(56) References Cited

U.S. PATENT DOCUMENTS

| 5,178,019 A | 1/1993 | Keiter |
|---|---|---|
| 5,287,758 A | 2/1994 | Manfred et al. |

(Continued)

FOREIGN PATENT DOCUMENTS

| CN | 1502041 A | 6/2004 |
|---|---|---|
| DE | 4102336 A1 | 8/1992 |

(Continued)

OTHER PUBLICATIONS

"Australian Application Serial No. 2016232703, Voluntary Amendment filed Oct. 10, 2017", 14 pgs.

(Continued)

*Primary Examiner* — Matthew D Krcha
(74) *Attorney, Agent, or Firm* — Schwegman Lundberg & Woessner, P.A.

(57) ABSTRACT

Embodiments of a dispenser and a dispensing method for an analyzer are disclosed herein. The dispenser can include a first structure containing a first fluid path and a probe containing a second fluid path. The first structure can include a heat source that can heat the first structure and a fluid contained in the first structure. The first structure can be physically and thermally connected to the probe such that the probe is indirectly heated by the heat source via thermal energy transferred through the first structure. The heat source can be controlled to heat the first structure to a first desired temperature and/or temperature range, which can result in the heating of the probe and the fluid contained in the probe to a second desired temperature and/or temperature range.

20 Claims, 25 Drawing Sheets

(52) U.S. Cl.
 CPC ............. *G01N 2035/00425* (2013.01); *G01N 2035/1048* (2013.01)

(56) References Cited

U.S. PATENT DOCUMENTS

| | | | |
|---|---|---|---|
| 5,365,798 A * | 11/1994 | Kressirer | ............ B01F 11/0088 366/140 |
| 5,960,160 A | 9/1999 | Clark et al. | |
| 6,260,407 B1 | 7/2001 | Petro et al. | |
| 6,945,638 B2 | 9/2005 | Teung et al. | |
| 7,850,921 B2 | 12/2010 | Iguchi et al. | |
| 9,415,404 B2 | 8/2016 | Toh et al. | |
| 9,423,803 B2 | 8/2016 | Dunfee et al. | |
| 9,745,184 B2 | 8/2017 | Keyes et al. | |
| 9,821,305 B2 | 11/2017 | Michels et al. | |
| 2002/0153055 A1* | 10/2002 | Downs | ................ B01F 13/1055 506/40 |
| 2005/0095723 A1* | 5/2005 | DiTrolio | ................. B01L 3/021 436/180 |
| 2007/0183945 A1 | 8/2007 | William et al. | |
| 2013/0195718 A1 | 8/2013 | Thorsten et al. | |
| 2015/0044664 A1 | 2/2015 | Sullivan et al. | |
| 2015/0323220 A1 | 11/2015 | Dumitrescu | |
| 2017/0319040 A1 | 11/2017 | Whitbread et al. | |
| 2018/0017200 A1 | 1/2018 | Keough et al. | |

FOREIGN PATENT DOCUMENTS

| | | |
|---|---|---|
| EP | 1380844 A2 | 1/2004 |
| EP | 2856039 A1 | 4/2015 |
| EP | 2940477 A1 | 11/2015 |
| EP | 3271074 A1 | 1/2018 |
| JP | 2005337967 A | 12/2005 |
| WO | WO-2013169841 A1 | 11/2013 |
| WO | WO-2014139535 A1 | 9/2014 |
| WO | WO-2016149666 A1 | 9/2016 |
| WO | WO-2017196952 A1 | 11/2017 |

OTHER PUBLICATIONS

"Chinese Application Serial No. 201680028227.4, Office Action dated Jun. 25, 2019", w/ English Translation, 17 pgs.

"European Application Serial No. 16714676.0, Communication Pursuant to Article 94(3) EPC dated Jul. 16, 2018", 5 pgs.

"European Application Serial No. 16714676.0, Communication Pursuant to Article 94(3) EPC dated Oct. 16, 2019", 5 pgs.

"European Application Serial No. 16714676.0, Response filed Jan. 28, 2019 to Communication Pursuant to Article 94(3) EPC dated Jul. 16, 2018", 12 pgs.

"European Application Serial No. 16714676.0, Response filed May 15, 2018 to Communication Pursuant to Rules 161(1) and 162 EPC dated Nov. 6, 2017", 24 pgs.

"Olympus AU3000i Service Manual Part C", Olympus America Inc, (2005), 5 pgs.

PCT/US2016/023255 filed received an IPRP dated Sep. 28, 2017, 8 pages.

PCT/US2016/023255 filed Mar. 18, 2016, received an ISR/WO dated Jun. 9, 2016, 13 pages.

"Brazilian Application Serial No. 1120170194554, Office Action dated Dec. 9, 2019", 4 pgs.

* cited by examiner

DISPENSER FOR AN ANALYZER

CROSS-REFERENCES TO RELATED APPLICATIONS

This application is a US National Phase of PCT Application No. PCT/US2016/023255, filed on Mar. 18, 2016, claims the benefit of U.S. Provisional Application No. 62/135,580, entitled "DISPENSER FOR AN ANALYZER," and filed on Mar. 19, 2015, the entirety of which are hereby incorporated by reference herein.

BACKGROUND OF THE INVENTION

The performing of assays can involve the application of one or several fluids, such as wash buffers, reagents, and diluents, to a sample. Many assay steps are temperature dependent, as measurements may change based on the temperature of the assay reaction mixtures through the time course of the assay. Assay precision thus depends on a consistent temperature profile for each instance of the assay. Many assays also determine results by comparing measurements from different instances of an assay where some of the instances include measurement of known concentration calibrators. As a result, assay accuracy may also depend on a consistent temperature profile for each instance of the assay. Consistent temperature profiles for each instance of the assay help ensure precise and accurate assay results. In some assays, it may be desirable to maintain a constant temperature. However, the temperature of the sample, of the fluids, of the equipment performing the assay, or of the room in which the assay is performed can affect the assay reaction temperature, and change the temperature profile for different instances of an assay.

Maintaining the temperature of the assay reaction mixture within a desired range and/or at a desired temperature can be difficult as the volume of fluid applied to the sample may vary between steps and the steps of different assays performed on the same equipment may differ. The different types of fluids can be stored at different temperatures. Reagents may be stored at chilled temperatures in a refrigerated compartment, while wash buffers may be stored at room temperature. Thus, when the equipment performing the assay has to dispense reagents, wash buffers, or both, it can be beneficially able to dispense these fluids at temperatures that do not affect the assay reaction temperature. If an assay requires an assay reaction mixture temperature of approximately 37° C., then the chilled reagents and the room temperature wash buffers may be heated up to, and dispensed at, approximately 37° C.

Fluid may need to be rapidly dispensed to a series of assays, or alternatively, there may be extended periods of time between assays. In a high throughput assay system that processes hundreds of assays per hour, the fluid may need to be dispensed every few seconds to a series of assays. Alternatively, within the same assay, wash buffer fluid may need to be dispensed and aspirated every few seconds to the same sample in a multi-step wash sequence. When there are extended periods of time between assays, and thus between applications of a fluid to a sample, the temperature of the fluid may vary from the desired temperature and/or temperature range and/or can approach the ambient temperature of the room in which the assay is being performed. When a conventional dispenser is idle for an extended period of time, the probe and the pre-heated fluid contained in the probe can cool to and remain at the ambient temperature. For example, when a conventional dispenser is idle for approximately seven minutes, then the fluid contained in the probe, which was pre-heated to approximately 37° C., can cool to and remain at an ambient temperature of approximately 18° C. Thus, the pre-heated fluid contained in the probe has lost most of its heat energy to its surrounding environment.

Several techniques have been used to maintain a desired temperature and/or temperature range of the fluid. These include maintaining the ambient temperature of the room in which the assay is performed at the desired temperature and/or within the desired temperature range and/or heating the fluid via, for example, one or several tube heaters. While the fluid has been heated, previous designs have been unable to maintain the desired temperature of the fluid throughout the dispenser, including at the point of dispense, and over extended periods of time. These problems have been addressed by "back-drawing" fluid into heated portions of the dispenser and/or purging some of the fluid from the dispenser.

While the currently used techniques for maintaining the fluid at the desired temperature can be effective, they also have several disadvantages. Specifically, the maintenance of the ambient temperature of the room at the desired temperature and/or within the desired temperature range can be difficult and expensive, "back-drawing" the fluid can decrease the accuracy of the dispensed fluid volume by precipitating gases in the fluid column and throughput is decreased by the "back-drawing" and reheating of the fluid, and purging can decrease throughput and result in wasted fluid and costs associated therewith. Further, "back-drawing" and purging may require additional hardware, such as longer tubing or a reservoir for handling purged fluids, which would render a compact design difficult.

BRIEF SUMMARY OF THE INVENTION

One aspect of the present disclosure relates to a dispenser for an analyzer. The dispenser includes a first structure that includes a first fluid pathway. In some embodiments, the first fluid pathway can contain fluid. The dispenser can include a probe that can include an inlet and an outlet. In some embodiments, the probe can contain fluid, and in some embodiments, the inlet of the probe in fluid can be in communication with the first fluid pathway. The dispenser can include a heat source in thermal communication with the first structure and the probe. In some embodiments, the heat source can be suitable for heating the first structure to a first pre-selected temperature range and the probe to a second pre-selected temperature range.

In some embodiments, a portion of the first fluid pathway has a helical configuration, and in some embodiments, the first structure further has a heatable inner structure and an outer structure, the heatable inner structure has a plurality of grooves, and the outer structure surrounds the heatable inner structure such that the outer structure and the plurality of grooves cooperate to form the helical configuration in the portion of the first fluid pathway. In some embodiments, the heat source is coupled to the first structure, no heat source is coupled to the probe (i.e. the heat source is not coupled to the probe), and the probe is coupled to the first structure to conduct heat from the first structure.

In some embodiments, the first pre-selected temperature range is 35 to 38 degrees Celsius. In some embodiments, the first pre-selected temperature range is the same as the second pre-selected temperature range. In some embodiments, the probe and the first structure have a thermal resistance of at least approximately 6.5 Kelvin per Watts (K/W). In some embodiments, the probe is made of a material selected comprising at least one of nickel, nickel alloy, aluminum, stainless steel, heat conductive plastic, and a material having a thermal conductivity of at least 70 watts per meters Kelvin (W/mK).

In some embodiments, the probe further has a height and a wall thickness, and in some embodiments, a ratio of the height to the wall thickness can be approximately 67.5, approximately 136, approximately 136.15, between 50 and 150, between 60 and 70, between 130 and 140, and/or any other or intermediate ratio. In some embodiments, the probe further has a height, a proximal wall thickness, and a distal wall thickness, and in some embodiments, a ratio of the height to the proximal wall thickness is approximately 4.81 and a ratio of the height to the distal wall thickness is approximately 19.5.

One aspect of the present disclosure relates to a dispenser for an analyzer. The dispenser can include a heatable structure that includes an inlet, an outlet, and a fluid pathway. In some embodiments, inlet of the heatable structure can receive a minimum dispense volume of fluid. The dispenser can include a probe that includes an inlet and an outlet, the inlet of the probe in fluid communication with the outlet of the heatable structure. In some embodiments, the probe can contain at least a first portion of the minimum dispense volume of fluid, and the outlet of the probe can dispense the minimum dispense volume of fluid within a first pre-selected temperature range. The dispenser can include a heat source in thermal communication with the heatable structure and the probe.

In some embodiments, the heat source is suitable for heating the first portion of the minimum dispense volume at the outlet of the probe to a second pre-selected temperature range and a second portion of the minimum dispense volume at the outlet of the heatable structure to the first pre-selected temperature range. In some embodiments, the dispenser is suitable for dispensing a minimum dispense volume at a pre-selected period between dispenses.

In some embodiments, a portion of the fluid pathway has a helical configuration, the heatable structure further has a heatable inner structure and an outer structure, the heatable inner structure has a plurality of grooves, and the outer structure surrounds the heatable inner structure such that the outer structure and the plurality of grooves cooperate to form the helical configuration in the portion of the fluid pathway. In some embodiments, the heat source is coupled to the heatable structure, no heat source is coupled to the probe (i.e. the heat source is not coupled to the probe), and the probe is coupled to the heatable structure to conduct heat from the heatable structure. In some embodiments, the fluid pathway can contain at least a second portion of the minimum dispense volume of fluid, and the first portion of the minimum dispense volume of fluid contained in the probe is less than the second portion of the minimum dispense volume of fluid contained in the fluid pathway.

In some embodiments, the probe can aspirate fluid through the outlet of the probe. In some embodiments, the dispenser further includes a temperature controller for regulating the first pre-selected temperature range and the second pre-selected temperature range. In some embodiments, the first pre-selected temperature range is 35 to 38 degrees Celsius.

One aspect of the present disclosure relates to a method for dispensing fluid to an analyzer. The method includes providing a minimum dispense volume to a fluid pathway of a heatable structure, heating, using a heat source in thermal communication with the heatable structure, the minimum dispense volume to a first pre-selected temperature range when the minimum dispense volume is contained at an outlet of the heatable structure, heating, using the heat source in thermal communication with a probe, the minimum dispense volume to a second pre-selected temperature range when the minimum dispense volume is contained in the probe, and dispensing, at an outlet of the probe, the minimum dispense volume within the first pre-selected temperature range at a pre-selected period between dispenses.

Further areas of applicability of the present disclosure will become apparent from the detailed description provided hereinafter. It should be understood that the detailed description and specific examples, while indicating various embodiments, are intended for purposes of illustration only and are not intended to necessarily limit the scope of the disclosure.

In the appended figures, similar components and/or features may have the same reference label. Where the reference label is used in the specification, the description is applicable to any one of the similar components having the same reference label.

DETAILED DESCRIPTION OF THE INVENTION

Dispensers for an analyzer can include one or several features to facilitate in dispensing fluid at a desired fluid temperature and/or in a desired fluid temperature range. These features can further maintain this desired fluid temperature and/or desired fluid temperature range at a plurality of dispense rates, frequencies, and with a wide-range of dispense volumes without, for example, drawing-back and/or purging some or all of the dispense fluid.

In one embodiment, a dispenser can include a first structure that can include a first fluidic pathway, also referred to herein as a "first fluid pathway" and/or a "first fluid path." The first fluid path can be located within the first structure and can be in thermal communication with a heat source. This thermal communication can allow the heating of the fluid within the first fluid path by the heat source.

A probe can be connected to the first structure. The probe can include a second fluidic pathway, also referred to herein as a "second fluid pathway" and/or a "second fluid path." The probe can connect to the first structure such that the first and second fluid pathways connect to allow fluid to flow through the first fluid pathway and then through the second fluid pathway. Additionally, the probe can thermally connect to the first structure to thereby allow the heating of the probe indirectly by the heat source via the first structure. This thermal connection between the probe and the first structure can be such to maintain the probe at a desired probe temperature and/or within a desired probe temperature range. Fluid is dispensed at the outlet of the probe. Thus, the temperature of the fluid at the point of dispense can be maintained at a desired temperature and/or within a desired temperature range. In some embodiments, this desired probe temperature and/or desired probe temperature range can be the same as or different from the desired fluid temperature and/or the desired fluid temperature range.

Figure 1A:
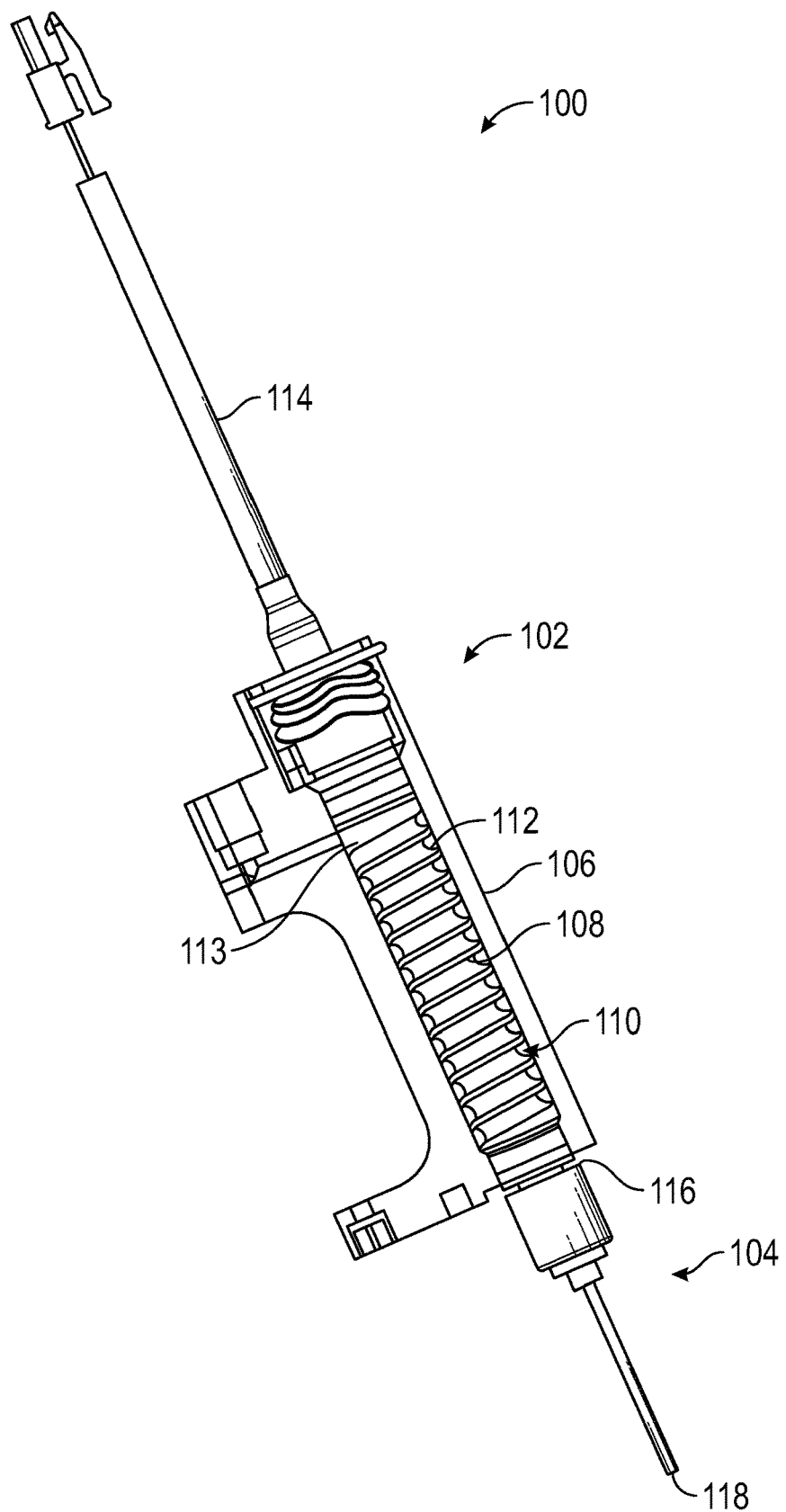
FIGS. 1A and 1B are side views of first embodiments of portions of a dispenser.
Figure 1B:
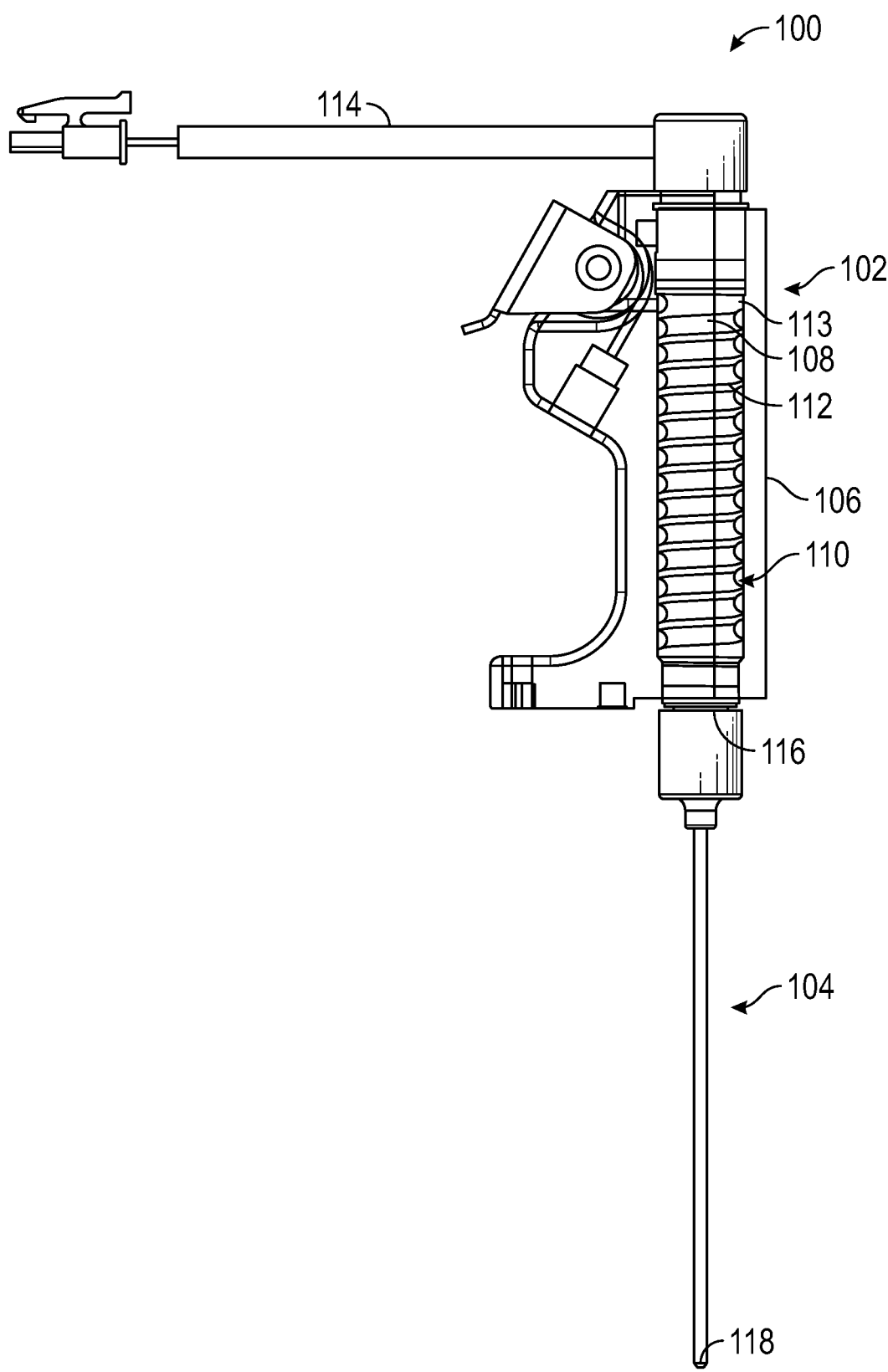

With reference now to FIGS. 1A and 1B, side views of first embodiments of portions of a dispenser 100 are shown. In some embodiments, the dispenser 100 can be part of an analyzer that can be used to analyze one or several samples. The dispenser 100 can be any desired type of dispenser including, for example, a wash buffer dispenser. The dispenser 100 can include one or several features configured to allow the dispensing of a desired volume of fluid at a desired rate, period between dispenses, and/or at a desired temperature. While parts of this invention describes the desired dispense volume of fluid in terms of a minimum dispense volume, the desired dispense volume of fluid can be, in the alternative, a maximum dispense volume, or any dispense volume between the minimum and the maximum dispense volume.

In the embodiments of FIGS. 1A-4B, the dispenser 100 can dispense a volume of from approximately 100 µl to approximately 500 µl, and/or any other intermediate volume, and can hold a total fluid volume of approximately 1035 µl. Alternatively, in the embodiment of FIGS. 5-7, the dispenser 100 can dispense a volume of from approximately 5 µl to approximately 2500 µl, and/or any other intermediate volume, and can hold a total fluid volume of up to 5000 µl.

The dispenser 100 can dispense a dispense volume at a pre-selected period between dispenses. The pre-selected period between dispenses can vary according to a desired throughput level. The dispenser 100 can dispense at a pre-selected period between dispenses of from approximately 9 seconds to infinity, from 1 second to 9 seconds, and/or any other intermediate value. When many assays need to be processed in a short amount of time, then the dispenser 100 can be configured to dispense approximately every 9 seconds, or any period less than 9 seconds. When running a high throughput condition, such as 400 tests per hour on the Beckman Coulter Unicel DxI 800 immunoassay system, the system's dispenser dispenses every 9 seconds. By contrast, when the assay system is idle, then the dispenser 100 may dispense only once in about 4 hours. The system can even be idle for more than 4 hours, such as during non-business hours.

The dispenser 100 can be configured to heat and dispense the fluid at a pre-selected temperature or temperature range. If the temperature profile of an assay requires the assay reaction mixture temperature to be approximately 37° C., then the dispenser may be configured to heat and dispense the fluid at a pre-selected temperature of approximately 37° C. In the embodiments of FIGS. 1A-4B, the dispenser 100 can heat and dispense the fluid at a pre-selected temperature of approximately 37° C.+/−0.7° C. In the embodiment of FIGS. 5-8, the dispenser 100 can heat and dispense the fluid at a pre-selected temperature of approximately 37° C.+/−2° C. Alternatively, temperature profiles of other assays may require different assay reaction mixture temperatures. Thus, in other embodiments, the dispenser 100 can dispense the fluid at approximately 20° C., approximately 30° C., approximately 35° C., approximately 37° C., approximately 37° C.+/−0.5° C., approximately 40° C., approximately 50° C., and/or any other intermediate value.

Figure 4A:
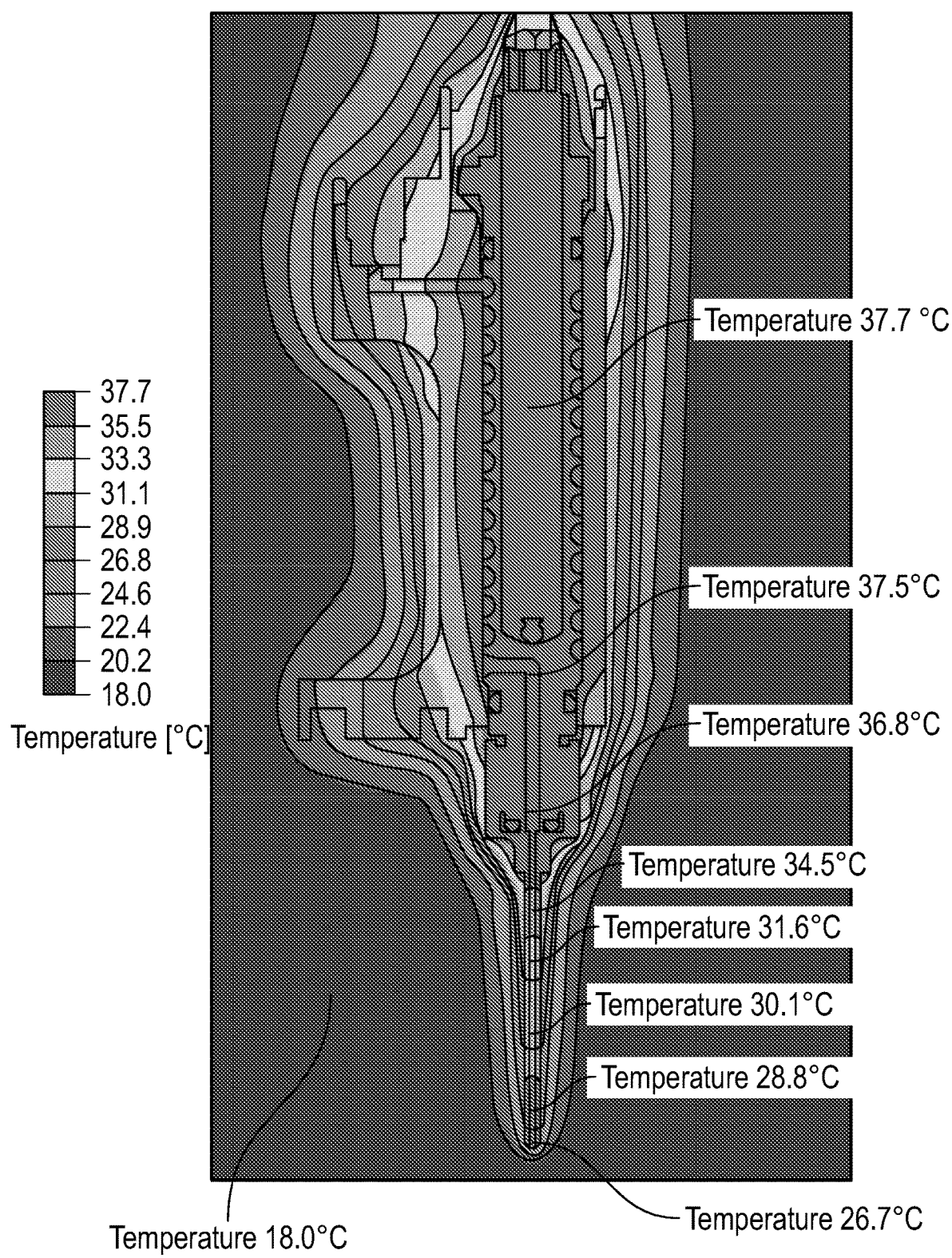
FIGS. 4A and 4B are schematic illustrations of first embodiments of the temperature distribution within a heated dispenser.
Figure 4B:
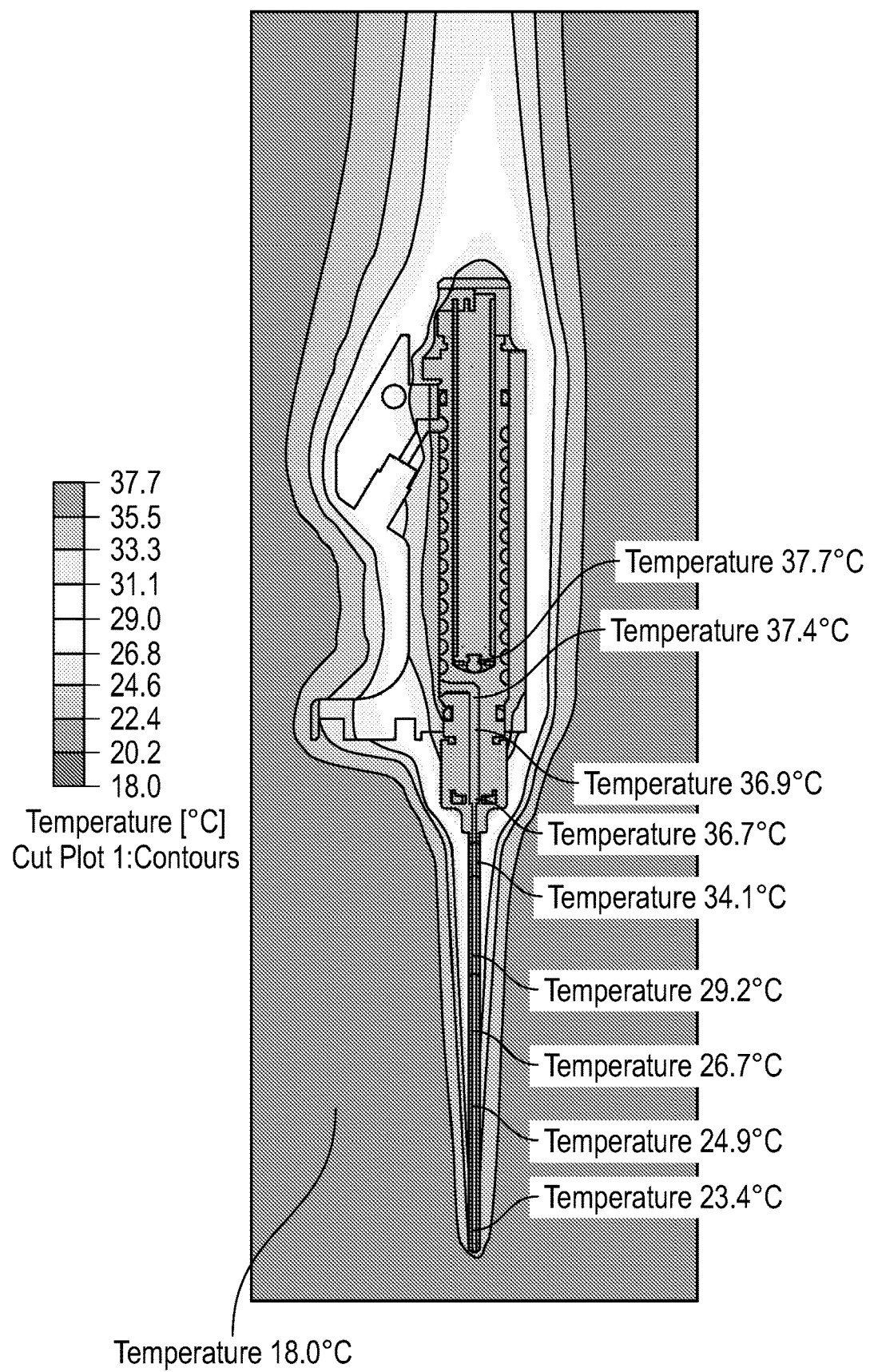
Figure 5:
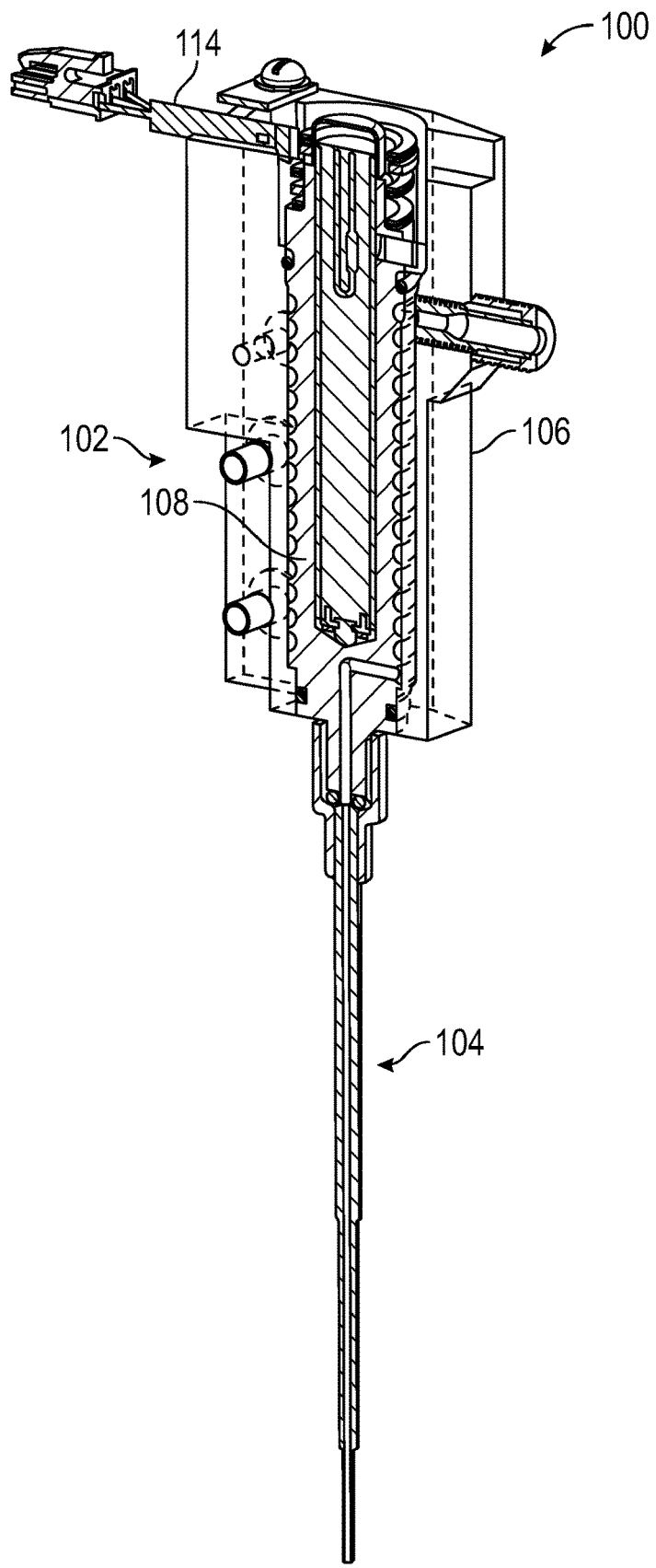
FIG. 5 is a section view of a second embodiment of a dispenser.
Figure 6:
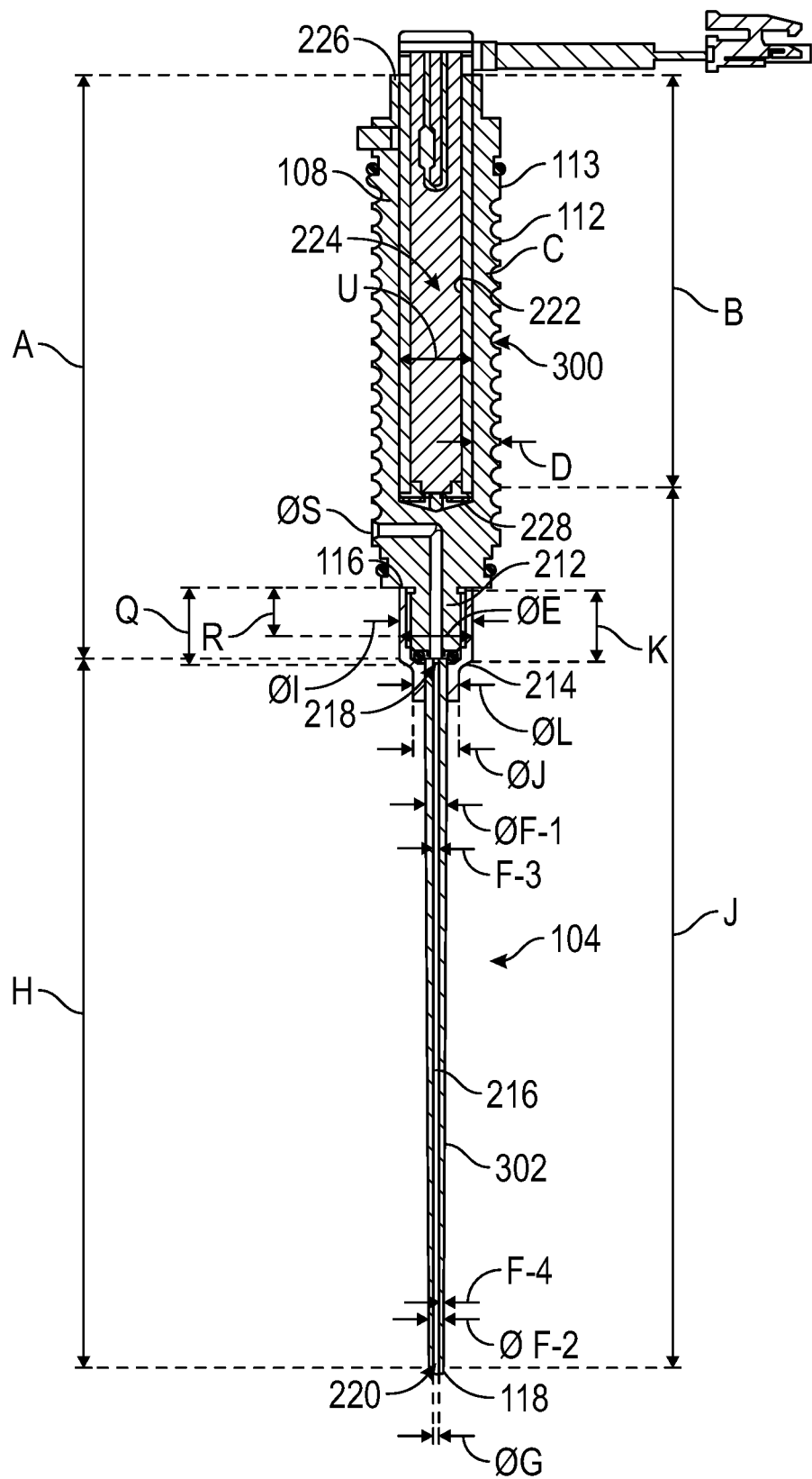
FIG. 6 is a section view of a second embodiment of a core and a probe of a dispenser.
Figure 7:
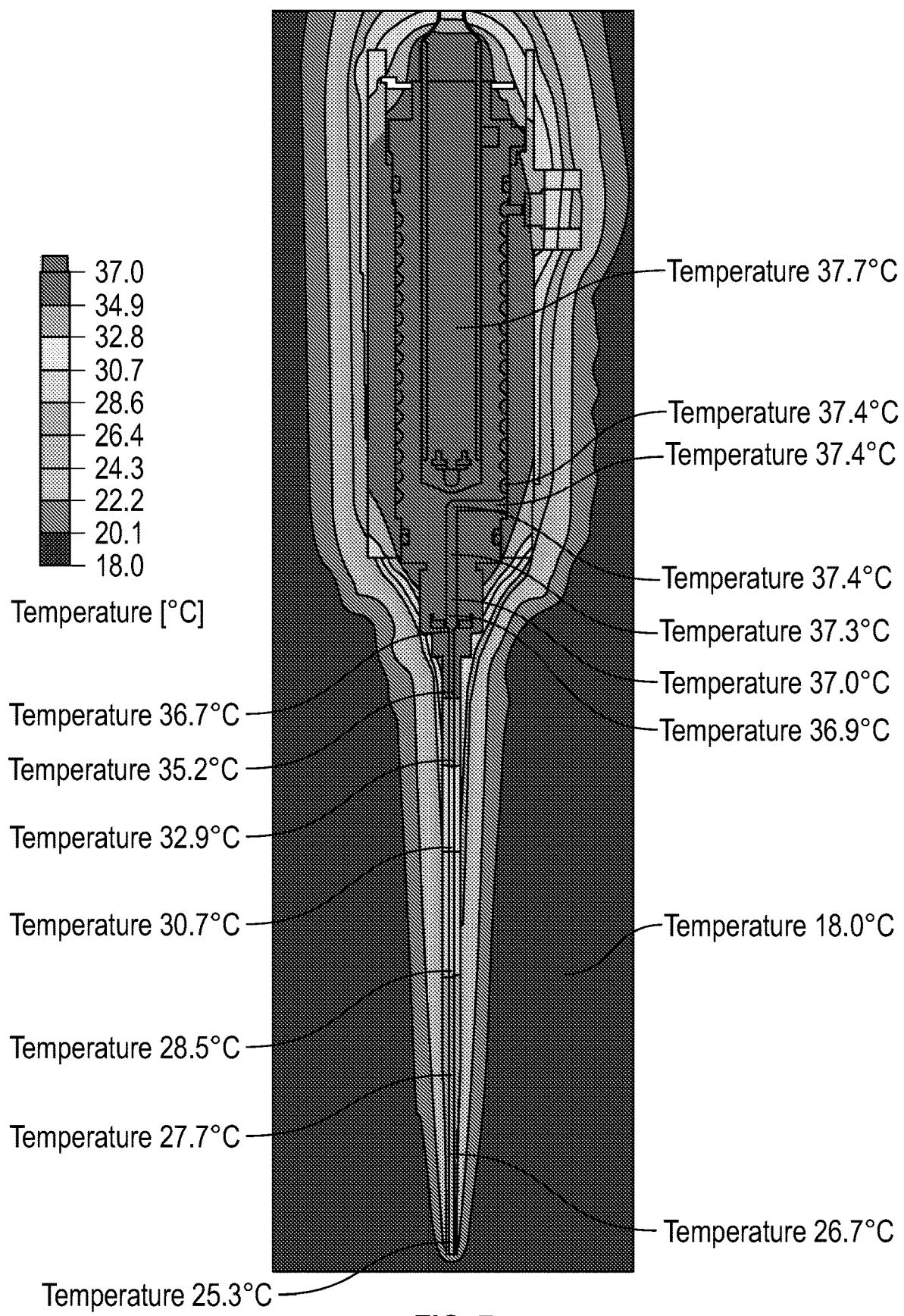
FIG. 7 is schematic illustration of one embodiment of the temperature distribution within a second embodiment of a heated dispenser.

The pre-selected temperature or temperature range can be configured by, for example, setting a heat source set point of the heat source 230. The heat source 230 is suitable for heating the first structure to the first pre-selected temperature range and the probe to a second pre-selected temperature range by setting its set point to a temperature within the first pre-selected temperature range. In the embodiments of FIGS. 1A-4B, the set point of heat source 230 can be set to approximately 37.7° C. to heat the first structure to a first pre-selected temperature range of approximately 36-38° C. and the probe to a second pre-selected temperature range of approximately 26-36° C. In the embodiment of FIGS. 5-7, the set point of heat source 230 can be set to approximately 37.7° C. to heat the first structure to a first pre-selected temperature range of approximately 36-38° C. and the probe to a second pre-selected temperature range of approximately 25-36° C.

In some embodiments, the fluid can be dispensed at a temperature of approximately 20° C., approximately 30° C., approximately 35° C., approximately 37° C., approximately 40° C., approximately 50° C., approximately 60° C., approximately 75° C., at approximately 37° C.+/−0.5° C., at approximately 37° C.+/−0.7° C., and at approximately 37° C.+/−2° C., and/or any other or intermediate temperature or range of temperatures. Thus, by way of example, the dispenser 100 can heat and dispense the fluid at a pre-selected temperature of approximately 55° C. The set point of heat source 230 can be set to approximately 55° C. to heat the first structure at a pre-selected temperature range of approximately 55° C.+/−2° C. and the probe to a second pre-selected temperature range of approximately 55° C.+/−15° C., thereby causing the dispenser 100 to dispense the fluid at a pre-selected temperature range of approximately 55° C.+/−2° C. Similarly, by way of further examples, the dispenser 800 can heat and dispense the fluid at a pre-selected temperature of approximately 55° C. The set point of heat source 900 can be set to approximately 55° C. to heat the first structure at a pre-selected temperature range of approximately 55° C.+/−2° C. and the probe to a second pre-selected temperature range of approximately 55° C.+/−15° C., thereby causing the dispenser 100 to dispense the fluid at a pre-selected temperature range of approximately 55° C.+/−2° C.

In some embodiments, one or several of these temperatures can correspond to a heat source set point. As used herein, "approximately" refers to a value of within 10% of the therewith associated value.

The dispenser 100 can include a heating module 102, also referred to herein as a "first structure" or a "heatable structure," and a probe 104. The first structure 102 can be configured to allow heating of fluid contained in one or both of the first fluid pathway in the first structure 102 and a second fluid pathway in the probe 104 to a pre-selected temperature and/or to within a pre-selected temperature range. A fluid contained in one or both of the first and second fluid pathways can be fluid that is static or dynamic. Thus, the first structure 102 can heat and maintain fluid that is static or dynamic. When the dispenser 100 is in the process of dispensing, aspirating, or exchanging fluid, the fluid contained in one or both of the first and second fluid pathways can be dynamic. Alternatively, when the dispenser 100 is in between dispenses or aspirations, the fluid contained in the one or both of the first and second fluid pathways can be static. Thus, fluid contained in the fluid pathways can be dynamic or static.

In embodiments in which the fluid is contained in the first and second fluid pathways, fluid contained in the first fluid pathway can be referred to as a first fluid portion, and fluid located in the second fluid pathway can be referred to as a second fluid portion. In some embodiments, fluid dispensed from the dispenser 100 can include a combination of the first and second fluid portions, and in some embodiments, the dispensed fluid can include more fluid from the first portion in the first fluid pathway than from the second fluid portion in the second fluid pathway. In some embodiments, this first fluid pathway can include an inlet through which fluid enters the first fluid pathway and the first structure 102, and an outlet through which fluid exits the first fluid pathway and the first structure 102.

As shown in FIGS. 1A and 1B, the first structure 102 includes a housing 106. The housing 106 can comprise a variety of shapes and sizes and can be made from a variety of materials. In some embodiments, all or portions of the housing 106 may contact fluid contained in the first structure 102. In such an embodiment, housing 106 can be made from a material that is non-reactive with the fluid. Alternatively, in some embodiments, the fluid can be contained so as to not contact the housing 106. In such an embodiment, the material of the housing 106 is not constrained by potential or actual reactivity with the fluid. In the embodiment depicted in FIG. 1, the housing 106 can be made from a polymer such as, for example, polycarbonate or acrylic. In one embodiment, the housing 106 can comprise a clear cast acrylic having a thermal conductivity of 0.20 W/mK.

The housing 106 can include a core 108. The core 108 can comprise a variety of shapes and sizes. In some embodiments, the core 108 can be an elongate member that can be, for example, cylindrical. In some embodiments, the core 108 can be positioned with respect to the housing 106 such that one or several spaces exist between the housing 106 and the core 108. These spaces can define the first fluid pathway 110. In some embodiments, these one or several spaces can be defined by one or several ridges 112 located on an exterior wall 113 of the core 108. These ridges 112 can be sized and shaped to engage, for example, to sealingly engage, with the housing 106 to define the one or several spaces that form the first fluid pathway 110. In some embodiments, the ridges 112 extend around all or portions of the exterior wall 113 of the core 108, and as seen in the first embodiments of FIGS. 1A and 1B, in some embodiments, some or all of the ridges 112 helically wrap around the exterior wall 113 of the core 108, and some or all of the first fluid pathway 110 can likewise helically wrap around the exterior wall 113 of the core 108, which can, for example, give the first fluid pathway 110 a helical configuration.

The embodiments of FIGS. 1-7 show a first fluid pathway 110 having a helical configuration. The helical configuration is advantageous because it allows more fluid to be contained in the first fluid pathway 110 compared to a fluid pathway configured as a straight cylindrical tube having the same diameter. Thus, compared to a straight cylindrical tube having the same diameter, the helical configuration maximizes the surface area in the first structure. The helical configuration is also advantageous because there is minimal to no dead space that will not be swept during aspiration and dispense. This avoids retention of pockets of fluid that might contaminate later transfers.

The core 108 can comprise a variety of shapes and sizes, and can be made from a variety of materials. In some embodiments, the material for the core 108 can be selected based on one or several material properties, including, for example, reactivity, thermal conductivity, or the like. In some embodiments, all or portions of the core 108 may contact fluid contained in the first structure 102. In the embodiments of FIGS. 1-7, the fluid contained in the first fluid pathway 110 is in contact with the core 108, which enables heat transfer from the core 108 to the fluid contained in the first fluid pathway 110. In some embodiments, the core 108 can be made from a material that is in contact with the fluid but is non-reactive with the fluid. Alternatively, in some embodiments, the fluid can be contained so as to not contact the core 108. In such an embodiment, the material for use in the core 108 is not constrained by potential or actual reactivity with the fluid.

In some embodiments, the thermal conductivity of the core 108 may affect the functioning of the dispenser 100, and a material may be selected that has a desired thermal conductivity so as to achieve a desired outcome. The core 108 can be made from nickel, nickel alloy, aluminum, stainless steel, heat conductive plastic, a material having a thermal conductivity of at least approximately 70 Watts per meter Kelvin (W/mK), a combination and/or alloy of the foregoing, and/or the like. Heat conductive plastic means plastic having a thermal conductivity of at least approximately 0.25 W/mK. For example, polyether ether ketone (PEEK) is a heat conductive plastic that has a thermal conductivity of approximately 0.25 W/mK. In the embodiments of FIGS. 1-7, the core 108 is made from nickel alloy, and in particular, Nickel 200 alloy, which exhibited a thermal conductivity of approximately 70.3 W/mK, a density of approximately 8.9 g/cm$^3$, and a specific heat of approximately 456 J/kg° C. For the embodiments of FIGS. 1A-4B, with the core 108 made of Nickel 200 alloy, the dispenser 100, operating in an ambient temperature of approximately 18° C., can dispense, for example, approximately 500 µl, at a pre-selected period between dispenses of approximately once per 9 seconds, or any period between 1 second to 9 seconds, and at a pre-determined temperature of approximately 37° C.+/−0.7° C. For the embodiment of FIGS. 5-7, with the core 108 made of Nickel 200 alloy, the dispenser 100, operating in an ambient temperature of approximately 18° C., can dispense, for example, approximately 500 µl, at a pre-selected period between dispenses of approximately once per 9 seconds, or any period between 1 second to 9 seconds, and at a pre-determined temperature of approximately 37° C.+/−2° C.

In the embodiments of FIGS. 1-7, the first fluid pathway 110 having a helical configuration is enclosed by a combination of the core 108 and the housing 106, as shown in FIGS. 1A-2B and 5. For the embodiments of FIGS. 1A-4B, with the core 108 made of Nickel 200 alloy, the portion of the core 108 that is in contact with the fluid contained in the first fluid pathway 110 can achieve a heat transfer coefficient, with water at approximately 18° C., of approximately 7.5 W/m²K in static state and approximately 2,215.1 W/m²K in dynamic state. For the embodiment of FIGS. 5-7, with the core 108 made of Nickel 200 alloy, the portion of the core 108 that is in contact with the fluid contained in the first fluid pathway 110 can achieve a heat transfer coefficient, with water at approximately 18° C., of approximately 8.0 W/m²K in static state and approximately 8,155.4 W/m²K in dynamic state. For the embodiments of FIGS. 1-7, with the housing 106 made of acrylic, the portion of the acrylic that is in contact with the fluid contained in the first fluid pathway 110 can achieve a heat transfer coefficient, in static state, ranging from approximately 5.035 W/m²K to approximately 6.92 W/m²K.

The first structure 102 can further include a cable 114 that can include one or several wires that can be used to power the dispenser and/or to send/receive signals from the dispenser 100 such as, for example, one or several control signals, sensing signals, or the like.

The probe 104 can receive fluid from the first structure 102 and can deliver the fluid. The probe 104 can comprise a variety of shapes and sizes and can be made from a variety of materials. The probe 104 can be made from nickel, nickel alloy, aluminum, stainless steel, heat conductive plastic, a material having a thermal conductivity of at least approximately 70 W/mK, a heat transfer coefficient of approximately 19 watts per square-meter Kelvin (W/m²K), a combination and/or alloy of the foregoing, and/or the like. In the embodiments of FIGS. 1-7, the probe 104 can be made from nickel alloy, and in particular, Nickel 200 alloy, which exhibited a thermal conductivity of approximately 70.3 W/mK, a density of approximately 8.9 g/cm³, and a specific heat of approximately 456 J/kg° C. For the embodiments of FIGS. 1A-4B, with the probe 104 made of Nickel 200 alloy, the probe 104 can achieve a heat transfer coefficient of approximately 19 W/m²K in static state. For the embodiment of FIGS. 5-7, with the probe 104 made of Nickel 200 alloy, the probe 104 can achieve a heat transfer coefficient of approximately 10 W/m²K in static state. For the embodiments of FIGS. 1A-4B, with the probe 104 made of Nickel 200 alloy, the dispenser 100, operating in an ambient temperature of approximately 18° C., can dispense, for example, approximately 500 µl, at a pre-selected period between dispenses of approximately once per 9 seconds, or any period between 1 second to 9 seconds, and at a pre-determined temperature range of approximately 37° C.+/−0.7° C. For the embodiment of FIGS. 5-7, with the probe 104 made of Nickel 200 alloy, the dispenser 100, operating in an ambient temperature of approximately 18° C., can dispense, for example, approximately 500 µl, at a pre-selected period between dispenses of approximately once per 9 seconds, or any period between 1 second to 9 seconds, and at a pre-determined temperature range of approximately 37° C.+/−2° C.

Alternatively, for the embodiment of FIGS. 5-7, the probe 104 can be made of stainless steel. Thus, in the embodiments of FIGS. 1A-4B, with the probe 104 made of stainless steel and the core 108 made of Nickel 200 alloy, the set point of heat source 230 can be set to approximately 37.7° C. to heat the first structure to a first pre-selected temperature range of approximately 36-38° C. and the probe to a second pre-selected temperature range of approximately 21.5-36° C.

The dimensions of the second fluid pathway in the probe are designed to approximate an ideal fin. An ideal fin is a long circular fin of uniform cross section exhibiting thermal properties of ideal heat transfer with no thermal resistance. The probe can be defined by a plurality of dimensions, as described further below.

An ideal fin can be defined by its fin efficiency and its fin effectiveness. Fin efficiency is a measure of an ideal fin's ability to conduct heat away from a heat source ($T_{base}$) to the ambient environment ($T_{amb}$). To measure the fin efficiency, the actual temperature gradient across the probe's second fluid pathway can be compared with the ideal temperature gradient across the probe's second fluid pathway. The ideal temperature gradient can exhibit thermal properties of ideal heat transfer with no thermal resistance. The ideal temperature gradient across the probe's second fluid pathway can be, for example, 1 because, in an ideal situation, the temperature at the inlet of the probe's second fluid pathway can be the same as the temperature at the outlet of the probe's second fluid pathway.

This fin efficiency can be determined according to the following equation, wherein:

$N_{fin}$ is the fin efficiency;
$m_{fin}$ is defined as:

$$m_{fin} = \sqrt{\frac{4 h_{probe}}{(k * d_{probe})}} ;$$

$h_{probe}$ is the heat transfer coefficient of the probe;
k is the thermal conductivity of the material of the probe;
$d_{probe}$ is the diameter of the probe;
$L_c$ is the critical length and is defined as:

$$L_C = L_{probe} + \frac{d_{probe}}{4} ;$$

$L_{probe}$ is the length of the probe.

$$N_{fin} = \frac{\tanh(m_{fin} * L_C)}{m_{fin} * L_C}$$

Fin effectiveness is a comparison of how much heat is being transferred from (1) a first structure to the probe versus (2) a first structure without the probe. A fin effectiveness greater than 1 is desired because it justifies having the probe coupled to the first structure. A fin effectiveness of 1 or less means that there is no difference between (1) a first structure coupled to the probe, and (2) a first structure not coupled to the probe, and thus, does not justify having the probe coupled to the first structure.

This fin effectiveness can be determined according to the following equation, wherein:

$E_{fin}$ is the fin effectiveness;
$T_h$ is the temperature of the fluid at the first temperature and/or temperature range;
$T_{amb}$ is the temperature of the fluid at the second temperature and/or temperature range;
$h_{probe}$ is the heat transfer coefficient or film coefficient of the probe;

$A_{base}$ is the area of the portion of the first structure to which the probe attaches;

$Q_{fin}$ is the amount of heat transferred to the probe.

$$E_{Fin} = \frac{Q_{fin}}{h_{probe} * A_{base} * (T_b - T_{amb})}$$

For the embodiments of FIGS. 1A-4B, when the probe 104 is made of Nickel 200 alloy, the probe 104 can exhibit a fin efficiency of approximately 0.79 and a fin effectiveness of approximately 69. A fin efficiency of approximately 0.79 means that the probe 104 can be approximately 79% as efficient as an ideal fin. A fin effectiveness of approximately 69 means that the effect of heat transfer is increased by approximately 69 times by including the probe 104 to the end of the first structure 102. For the embodiment of FIGS. 5-7, when the probe 104 is made of Nickel 200 alloy, the probe 104 can exhibit a fin efficiency of approximately 0.89 and a fin effectiveness of approximately 102. A fin efficiency of approximately 0.89 means that the probe 104 can be approximately 89% as efficient as an ideal fin. A fin effectiveness of approximately 102 means that the effect of heat transfer is increased by approximately 102 times by including the probe 104 to the end of the first structure 102.

The material of the core 108 and the probe 104 can, in some embodiments, also be compatible with the fluid. Wash buffer is a known oxidizer that may degrade the material of the core 108. Wash buffer can oxidize metals from the surface of the metal. The oxidized metals can then enter the fluid and cause an enzymatic reaction. Oxidized metals can react with emitted chemiluminescence and cause a false negative or a false positive in an assay result. Nickel 200 alloy exhibits excellent resistance to oxidation including at temperatures up to 315° C. Nickel 200 alloy has been shown to not react with wash buffer or significantly affect Lumi-Phos 500 substrate fluids.

In some embodiments, the probe 104 can have a proximal end 116 and a distal end 118, and a lumen, also referred to herein as a second fluid pathway, extending between the proximal end 116 and the distal end 118 of the probe 104. In the embodiments of FIGS. 1A-4B, the second fluid pathway of the probe 104 can hold a volume of approximately 54 µl. Alternatively, in the embodiment of FIGS. 5-7, the second fluid pathway of the probe 104 can hold a volume of approximately 80 µl. In other embodiments, the second fluid pathway of the probe 104 can hold volumes appropriate to the amount of fluid to be transferred of approximately 5 µl, approximately 10 µl, approximately 20 µl, approximately 30 µl, approximately 40 µl, approximately 50 µl, approximately 60 µl, approximately 70 µl, approximately 90 µl, approximately 100 µl, approximately 150 µl, approximately 200 µl, and/or any intermediate volume.

Figure 2A:
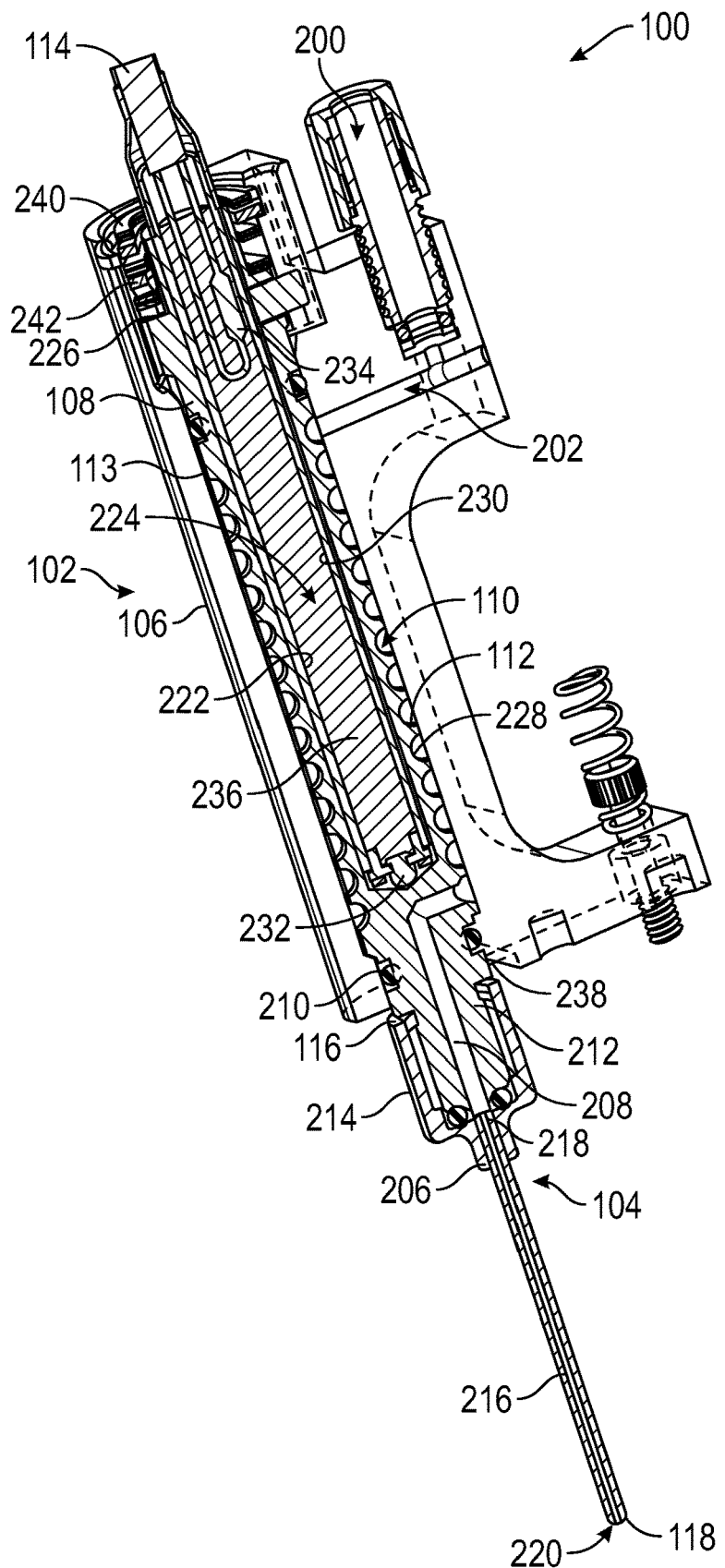
FIGS. 2A and 2B are section views of first embodiments of a dispenser.
Figure 2B:
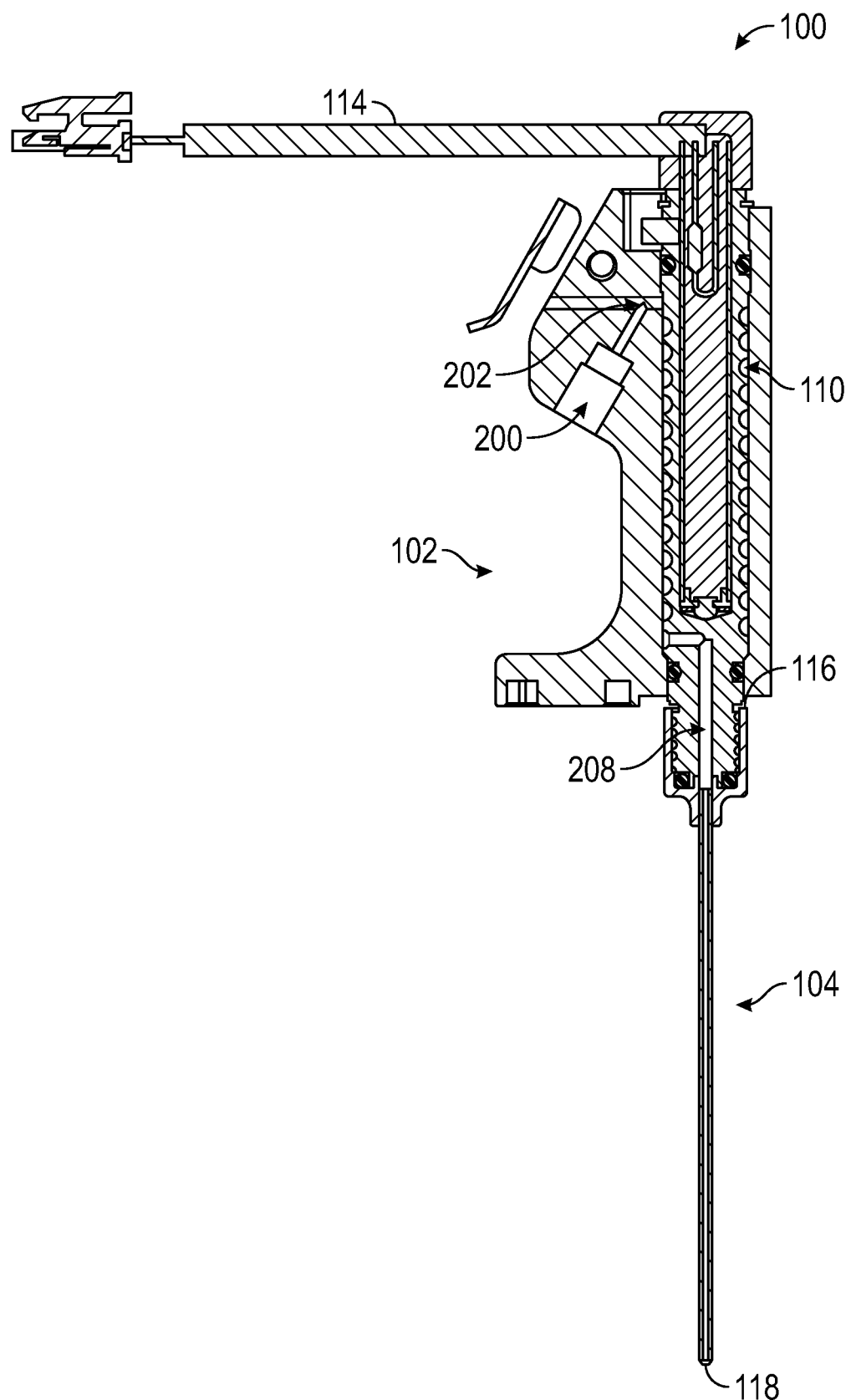

With reference now to FIGS. 2A and 2B, section views of first embodiments of the dispenser 100 is shown. As seen in FIGS. 2A and 2B, the dispenser 100 includes the first structure 102 including the housing 106 and the core 108. As discussed, the housing 106 and the core 108 together define the first fluid pathway 110 via ridges 112. The first fluid pathway 110 further includes inlet 200 located in the housing 106, an inlet channel 202 connecting the inlet 200 to the exterior wall 113 of the core 108, an outlet 206, and an outlet channel 208 connecting the outlet 206 to the exterior wall 113 of the core 108. A seal 210 extends between the core 108 and the housing 106 proximate to the outlet 206. The seal 210, which can be an O-ring or similar seal, can prevent the fluid from escaping from the first fluid pathway 110. When the connection portion 212 is connected to the connector 214 of the probe 104, the seal 210 is compressed so as to provide compliant feedback for the probe 104 to prevent the probe 104 from disconnecting from the connection portion 212 during normal vibration and operation.

The outlet 206 is located on a connection portion 212 that is part of the first structure 102, and specifically that is a part of the core 108. The connection portion 212 can connect to a connector 214 of the probe 204 to thereby fluidly connect the outlet 206 of the first fluid pathway 110 to the second fluid pathway 216 having an inlet 218 and an outlet 220. In some embodiments, the dispenser 100 can be configured to dispense fluid through the outlet 220, and/or in some embodiments, the dispenser 100 can be configured to aspirate fluid through the outlet 220. In such an embodiment, the dispenser 100 can be configured to aspirate from approximately 5 µl to approximately 500 µl, from approximately 25 µl to approximately 55 µl, and/or intermediate volume of fluid. In the embodiment of FIGS. 1A-7, the dispenser 100 can aspirate a volume of from approximately 5 µl to approximately 500 µl, and/or any intermediate volume of fluid.

In some embodiments, the connection portion 212 and the connector 214 can be sized, shaped, and/or designed to achieve a desired degree of heat transfer from the first structure 102 to the probe 104 such that when the first structure 102 is at a first temperature and/or in a first temperature range, the probe 104 is at a second temperature and/or in a second temperature range. In some embodiments, one or both of the first and second temperatures and/or temperature ranges can be pre-selected. In some embodiments, the first temperature and/or temperature range can be the same as the second temperature and/or temperature range, and in some embodiments, the first temperature and/or temperature range can be different from the second temperature and/or temperature range.

Figure 3A:
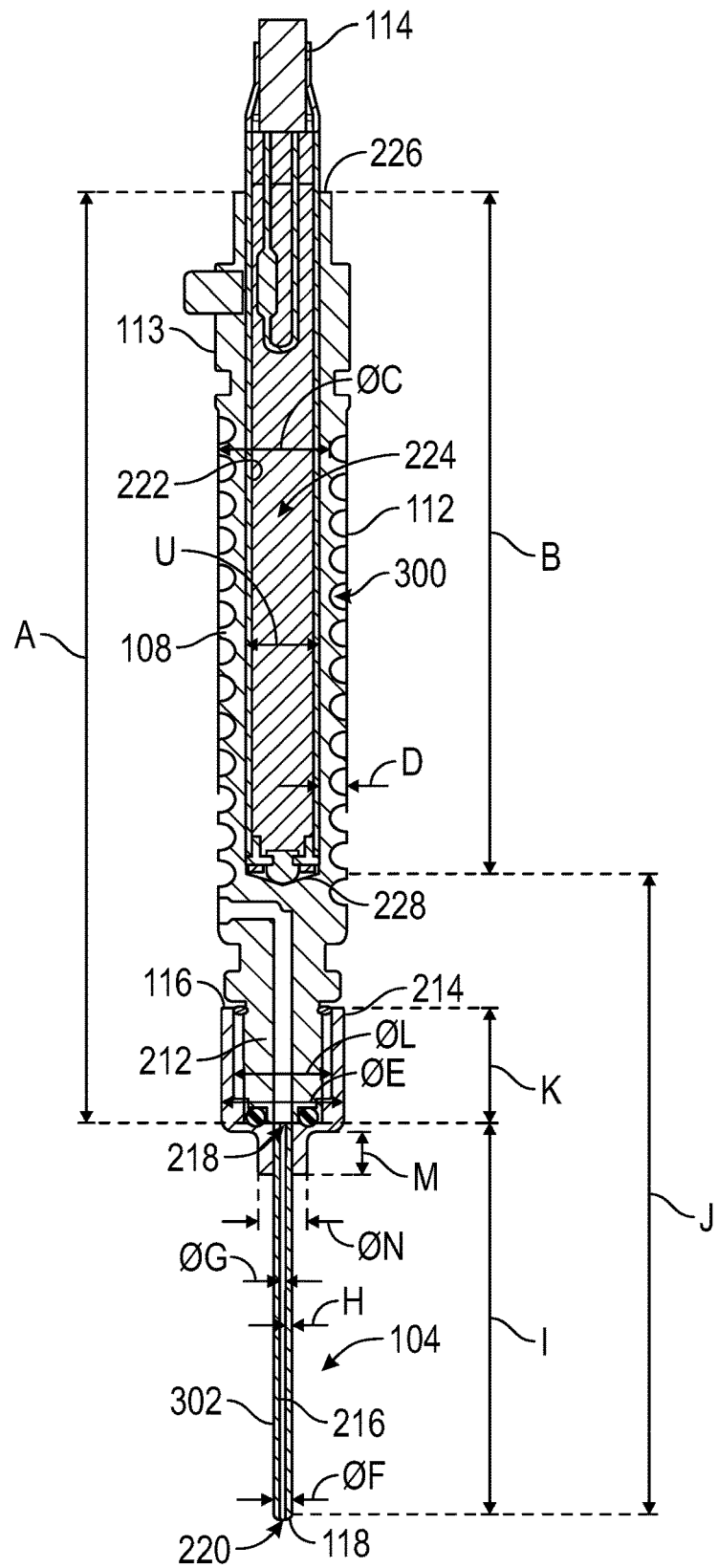
FIGS. 3A and 3B are section views of first embodiments of a core and a probe of a dispenser.
Figure 3B:
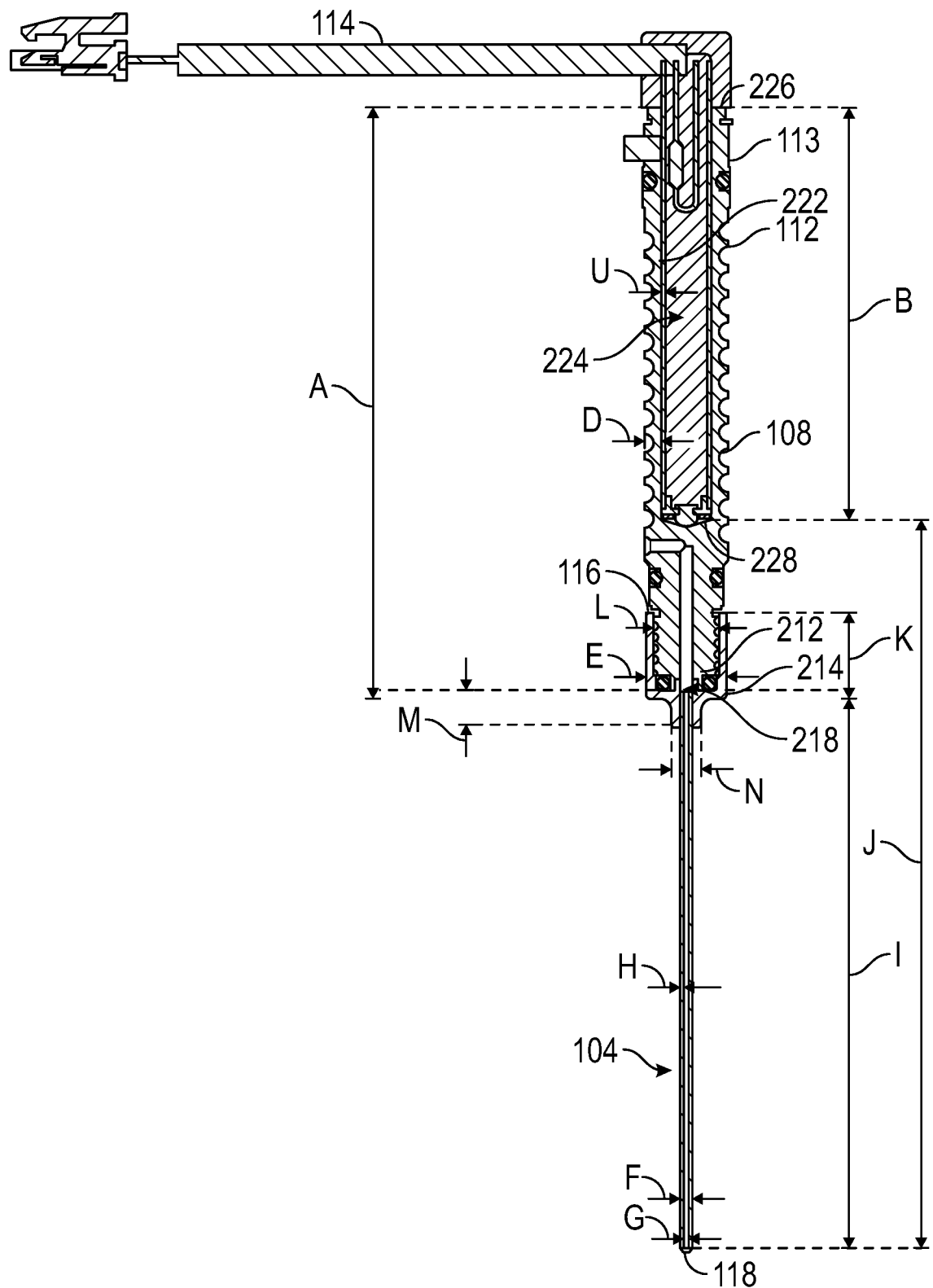

As shown in FIGS. 2A-3B, the connection portion 212 and the connector 214 can physically connect the probe 104 and the first structure 102, can fluidly connect the first fluid pathway 110 and the second fluid pathway 216, and can thermally connect the probe 104 and the first structure 102. The first structure 102 and the probe 104 can be connected by a threaded fitting of the connector 214 and the connection portion 212, such as a male and female threaded 5/16-18 UNC. As shown in FIGS. 2-3, the connector 214 mates with the connection portion 212 by a threaded fitting. The interior surface of the connector 214 has helical threads that mate with corresponding helical threads on the exterior surface of the connection portion 212 by way of rotation. In some embodiments, when the connector 214 is mated with the connection portion 212, the exterior surface of the connection portion 112 is in physical contact with the interior surface of the connector 214, which enables thermal conductivity between the first structure 102 and the probe 104. When the connector 214 is mated with the connection portion 212 by this threaded connection, the dispenser 100, operating in an ambient temperature of approximately 18° C., can dispense, for example, a dispense volume of approximately 500 µl, at a pre-selected period between dispenses of approximately 9 seconds, or any period between 1 second to 9 seconds, and at a pre-determined temperature of approximately 37° C.+/−2° C. Also, when the connector 214 is mated with the connection portion 212, then the outlet 206 of the first fluid pathway is in fluid communication with the inlet 218 of the second fluid pathway 216. The relevant dimensions of the connection portion 212 and the connector 214 are described further below with reference to FIGS. 3A and 3B.

Compared to a one-piece structure, having the first structure 102 and the probe 104 as separate but connectable structures, as articulated above, is advantageous because it improves serviceability. If the probe 104 becomes defective, then the user or maintenance personnel can replace only the probe, and not the entire dispenser. Replacing the entire dispenser can be difficult and time-consuming because it requires understanding how the dispenser is connected to the overall analyzer. Alternatively, other dispensers may include a probe embedded within the dispenser and to replace such probe, it requires understanding how the dispenser can be disassembled to remove such probe. The average user may not know how or have the time to replace or disassemble the dispenser, and thus, will require scheduled maintenance personnel, thereby losing time. Therefore, without having to replace or disassemble the entire dispenser, it results in improved serviceability by way of easier probe replacement, costs savings, and time savings.

As seen in FIGS. 2A and 2B, the core 108 can, in some embodiments, include an interior wall 222 that can define an internal volume 224 of the core 108 that can be, for example, an elongate internal volume 224 that can be closed at one end and open at the other. The internal volume 224 of the core 108 can have a top 226 proximate to the cable 114 and a bottom 228 proximate to the connection portion 212 of the core 108. As seen, the top 226 of the internal volume 224 is open and the bottom 228 of the internal volume 224 is closed.

The core 108 can include and/or connect to a heat source 230 that can heat the core 108 and indirectly heat the probe 104 via heat transfer from the core 108. In embodiments, the heat source 230 can be integrated into the core 108, and in some embodiments, the heat source 230 can be physically and/or thermally connected with the core 108. In the embodiments of FIGS. 1A-7, the heat source 230 is directly connected/coupled with the core 108, but the heat source 230 is not directly connected/coupled to the probe 104. The heat source 230 is in thermal communication with the probe 104 via the core 108, which enables the probe 104 to conduct heat from the core 108 and the heat source 230, from the heat source 230 via the core 108, or a combination thereof. This indirect heating of the probe 104 advantageously controls the temperature of probe 104 while limiting the diameter of probe 104 for compatibility with small diameter reaction vessels and other fluid containers. In other embodiments, the heat source 230 can be directly connected/coupled to the probe 104.

The heat sources 230 can comprise a variety of shapes, sizes, and types, and can be selected based on the ability/suitability of the heat source 230 to achieve the desired fluid temperature and/or fluid temperature range under a set of desired and/or expected operating conditions. In some exemplary embodiments, the heat source 230 can comprise a hydronic heat source, a resistance heat source, a heat pump, or the like. In one specific exemplary embodiment, and as shown in FIGS. 2A and 2B, the heat source 230 can comprise an etched foil resistance heater such as, for example, a 12 W etched foil resistance heater that can be located in the internal volume 224 of the core 108, and specifically can be affixed to the interior wall 222 of the core 108. In embodiments in which the heat source 230 is a resistance heat source, power for the heat source 230 can be provided via the cable 114.

In some embodiments, the internal volume 224 of the core 108 can also include a heat sensing element such as thermistor 232. The heat sensing element can be configured to detect the temperature of all or portions of the first structure 102. In some embodiments, the heat sensing element can be configured to detect the temperature of the portion of the first structure 102, and specifically, the portion of the core 108 proximate to the outlet 206. In some embodiments, the heat sensing element can be positioned at the bottom 228 of the internal volume 224 of the core 108 to enable the sensing of the temperature of the portion of the core 108 proximate to the outlet 206. The heat sensing element can be electrically connected to one or several of the wires in cable 114, and can be connected to a temperature controller that can be configured to regulate the temperature of one or both of the first structure 102 and the probe 104.

The internal volume 224 can further include a temperature cut-off (TCO) 234. The TCO 234 can be configured to detect a temperature of the heat source 230 and/or of one or several portions of the core 108 and/or of the first structure 102, and to affect the operation of the heat source 230 if the detected temperature exceeds a threshold value. In some embodiments, the TCO 234 can comprise a switch, such as, for example, a bi-metallic switch. In some embodiments, when the temperature measured by the TCO 234 exceeds a threshold value, power to the heat source 230 is decreased and/or cut. In some embodiments, the TCO 234 can be located proximate to the top 226 of the internal volume 224 of the core.

In some embodiments, the remaining portions of the internal volume 224 of the core 108 can be filled with an inner core 236. The inner core 236 can be configured to fill the remaining space within the internal volume 224 and thereby provide support to the components located in the internal volume 224 of the core 108 and to thermally connect the components located in the internal volume 224 of the core 108. In some embodiments, the inner core 236 can comprise one or several resins such as, for example, one or several epoxy resins. In one particular embodiment, the inner core 236 can comprise one or several heat-conductive epoxy resins.

The core 108 can be affixed and/or secured within the housing 106. In some embodiments, and as shown in FIG. 2A, the core 108 can be affixed and/or secured within the housing 106 via a first securement feature such as first snap-ring 238 located proximate to the outlet 206 of the core 108, a second securement features such as second snap-ring 240 located proximate to the top 226 of the internal volume 224, and a spring such as a wave-spring 242 located between the second snap-ring 240 and the top 226 of the internal volume 224. These features 238, 240, 242 can interact with each other and with the core 108 and the housing 106 to secure the core 108 within the housing 106.

With reference now to FIGS. 3A and 3B, section views of embodiments of a core 108 and the probe 104 are shown. The cores 108 shown in FIGS. 3A and 3B includes a plurality of ridges 112 located on exterior wall 113, which ridges define a plurality of grooves 300. In the embodiments of FIGS. 1A-4B, each groove 300 has a diameter of approximately 0.094 inches. The core 108 further includes an internal volume 224 defined by an interior wall 222 of the core 108, and having a top 226 and bottom 228. The core 108 further includes a connection portion 212 that connects with the connector 214 of the probe 104. The probe 104 includes the proximal end 116 comprising the inlet 218 proximate to the proximal end, the distal end 118 comprising the outlet 220 proximate to the distal end, and the second fluid pathway 216 comprising a lumen extending between the inlet 218 and the outlet 220.

In some embodiments, both the core 108 and the probe 104 are defined by a plurality of dimensions. In the embodiments of FIGS. 1A-4B, the core length A is approximately 2.8 inches, approximately 2.88 inches, approximately 3 inches, approximately 3.157 inches, between 1 and 5 inches, between 2 and 4 inches, between 2.5 and 3.5 inches, between 2.75 and 3 inches, between 3 and 3.5 inches, or any other or intermediate value or within any other or intermediate range. The internal volume of the core 108 can be defined by an internal volume length B measured from the top 226 to the bottom 228 of the internal volume. In the embodiments of FIGS. 1A-4B, the internal volume length B is approximately 2 inches, approximately 2.03 inches, approximately 2.033 inches, approximately 2.3 inches, approximately 2.310 inches, between 1 and 4 inches, between 2 and 3 inches, and/or any other or intermediate value or within any other or intermediate range. The core 108 can be further defined by a core diameter C. In the embodiments of FIGS. 1A-4B, the outer core diameter C is approximately 0.419 inches.

The core wall thickness D can be measured between the interior wall 222 and the exterior wall 113. In the embodiments of FIGS. 1A-4B, the core wall thickness D is approximately 0.082 inches without a groove diameter cut and is approximately 0.035 inches with a groove diameter cut. In the embodiments of FIGS. 1A-4B, the inner core diameter U is approximately 0.255 inches.

The probe 104 can be defined by a plurality of dimensions. The connector 214 can defined by a proximal outer connector diameter E, a proximal length K, a proximal inner diameter L, a distal outer connecter diameter N, a distal length M, and a distal inner connecter diameter F. The distal inner connector diameter F is approximately equal to the member diameter F of the elongate member 302, described below. In the embodiments of FIGS. 1A-4B, the proximal outer connect diameter E is approximately 0.4 inches, the proximal length K is approximately 0.39 inches, the proximal inner diameter L is approximately 0.25 inches, approximately 0.26 inches, approximately 0.39 inches, approximately 0.4 inches, between 0.25 and 0.5 inches, and/or any other or intermediate value or within any other or intermediate range, the distal outer connector diameter N is approximately 0.15 inches, the distal length M is approximately 0.15 inches, approximately 0.18 inches, between 0.1 and 0.2 inches, and/or any other or intermediate value or within any other or intermediate range, and the distal inner connector diameter F is approximately 0.062 inches. The probe 104 can include an elongate member 302 that defines the second fluid pathway 216. The elongate member 302 can have a member diameter F. In the embodiments of FIGS. 1A-4B, the member diameter F is approximately 0.062 inches, which matches the inner connector diameter F. The second fluid pathway 216 can have a second fluid pathway diameter G. In the embodiments of FIGS. 1A-4B, the second fluid pathway diameter G is approximately 0.022 inches. The elongate member 302 can have a wall thickness H. In the embodiment of FIGS. 1A-4B, the wall thickness H is approximately 0.02 inches. The elongate member 302 can have a member length I, measured from the inlet 218 to the outlet 220. In the embodiments of FIGS. 1A-4B, the member length I is approximately 1.25 inches, approximately 1.35 inches, approximately 1.5 inches, approximately 1.75 inches, approximately 2.0 inches, approximately 2.5 inches, approximately 2.723 inches, approximately 2.75 inches, approximately 3 inches, approximately 3.5 inches, between 1 and 4 inches, and/or any other or intermediate value or within any other or intermediate range. The length J is measured from the bottom 228 of the internal volume 224 of the core 108 to the outlet 220 of the probe 104. In the embodiments of FIGS. 1A-4B, length J is approximately 2.0 inches, approximately 2.20 inches, approximately 2.5 inches, approximately 2.75 inches, approximately 3.5 inches, approximately 3.57 inches, approximately 4 inches, between 1 and 5 inches, and/or any other or intermediate value or within any other or intermediate range. Thus, in the embodiments of FIGS. 1A-4B, the ratio of the member length I to the wall thickness H is approximately 60, approximately 67.5, approximately 100, approximately 130, approximately 130, approximately 136, approximately 136.15, approximately 150, and/or any other or intermediate value; the ratio of the member length I to the second fluid pathway diameter G is approximately 60, approximately 61.4 approximately 100, approximately 120, approximately 123.77, approximately 130, approximately 150, and/or any other or intermediate value; the ratio of the member length I to the member diameter F is approximately 20, approximately 21.8, approximately 30, approximately 40, approximately 32, approximately 43.19, approximately 50, and/or any other or intermediate value; and the ratio of the second fluid pathway diameter G to the member diameter F is approximately 2.82.

The connection portion 212 can be defined by a length K and an outer diameter L. The outer diameter L includes a plurality of helical threads. The length K of the connection portion 212 is approximately equal to the proximal length K of the connector 214, and the outer diameter L of the connection portion 212 is approximately equal to the proximal inner diameter L of the connector 214. Thus, when the connector 214 is mated with the connection portion 212, the exterior surface of the connection portion 112, defined by the length K and the outer diameter L of the connection portion 212, is in physical contact with the interior surface of the connector 214, defined by the proximal length K and the proximal inner diameter L of the connector 213.

The dimensions set forth above for A-N describe the exemplary embodiments of FIGS. 1A-4B. With these dimensions of A-N, the dispenser 100, operating in an ambient temperature of approximately 18° C., can dispense, for example, approximately 500 µl, at a pre-selected period between dispenses of approximately once per 9 seconds, or any period between 1 second to 9 seconds, and at a predetermined temperature of approximately 37° C.+/−0.7° C.

Due to the dimensions of the dispenser 100 and the placement of the heat source 230, different portions of the dispenser 100 can be maintained at different temperatures. This is depicted in FIGS. 4A and 4B, which show the first structure 102 at a first set of temperatures, and the probe 104, which is indirectly heated by the heat source 230 via the core 108, at a second set of temperatures. Specifically, in some embodiments, the core 108 proximate to the outlet 206 and/or the fluid exiting the outlet 206 can be at a first temperature and/or within a first temperature range, which first temperature and/or temperature range can be preselected, and the probe proximate to the outlet 220 and/or the fluid exiting the outlet 220 can be at a second temperature and/or within a second temperature range, which second temperature and/or temperature range can be preselected. In some embodiments, the first temperature and/or temperature range can be the same as the second temperature and/or temperature range, and in some embodiments, the first temperature and/or temperature range can be different from the second temperature and/or temperature range. In some embodiments, the first temperature range can be, for example, between approximately 35° C. and 38° C., and the second temperature range can be, for example, between 25° C. and 35° C. In some embodiments, the upper limit of the first temperature range can be no more than 15° C. higher than the lower limit of the second temperature range. In some embodiments, the dispenser can be operated at ambient temperatures of approximately 18° C. The design of the embodiment permits operation at a range of ambient temperatures with minimal effect on the controlled temperature ranges. A dispenser for an analyzer can operate in a range of ambient temperatures, from approximately 18° C. to approximately 36° C.

With reference now to FIG. 5, a section view of a second embodiment of the dispenser 100 is shown. This dispenser 100 includes the first structure 102 including the housing 106 and the core 108, and the probe 104. The components and materials of the dispenser 100 shown in FIG. 4 are the same as discussed in the embodiments above, but the size, shape, and/or position of some of those components are different.

With reference now to FIG. 6, a section view of a second embodiment of a core 108 and the probe 104 is shown. The core 108 shown in FIG. 6 includes a plurality of ridges 112 located on exterior wall 113, and an internal volume 224 defined by an interior wall 222 of the core 108, and having a top 226 and bottom 228. The core 108 further includes a connection portion 212 that connects with the connector 214 of the probe 104. As seen in FIG. 6, the probe 104 includes the proximal end 116 comprising the inlet 218 proximate to the proximal end, the distal end 118 comprising the outlet 220 proximate to the distal end, and the second fluid pathway 216 comprising a lumen extending between the inlet 218 and the outlet 220.

As seen in FIG. 6, both the core 108 and the probe 104 are defined by a plurality of dimensions. In the embodiment of FIGS. 5-7, the core length A is approximately 3.28 inches.

The internal volume of the core 108 can be defined by an internal volume length B measured from the top 226 to the bottom 228 of the internal volume. In the embodiment of FIGS. 5-7, the internal volume length B is approximately 2.4 inches. The core 108 can be further defined by an internal volume diameter C. In the embodiment of FIGS. 5-7, the internal volume diameter C is approximately 0.38 inches. The core wall thickness D is measured between the interior wall 222 and the exterior wall 113, and which can be either a minimum thickness or a maximum thickness. In the embodiment of FIGS. 5-7, the core wall thickness D is approximately 0.169 inches without a groove diameter cut and is approximately 0.122 inches with a groove diameter cut. The core 108 shown in FIG. 6 includes a plurality of ridges 112 located on exterior wall 113, which ridges define a plurality of grooves 300. In the embodiment of FIGS. 5-7, each groove 300 has a diameter of approximately 0.094 inches. In the embodiment of FIGS. 5-7, the inner core diameter U is approximately 0.38 inches.

The probe 104 can be defined by a plurality of dimensions. The connector 214 can be defined by a proximal outer connector diameter E, a proximal length Q, a proximal inner diameter I, a distal outer connecter diameter J, a distal length K, and a distal inner diameter inner connector diameter L. The distal inner connector diameter L is approximately equal to the first member diameter F-1 of the elongate member 302, described below. In the embodiment of FIGS. 5-7, the outer connector diameter E is approximately 0.4 inches, the proximal length Q is approximately 0.39 inches, the proximal inner diameter I is approximately 0.26 inches, the distal outer connecter diameter J is approximately 0.15 inches, the distal length K is approximately 0.15 inches, and the distal inner diameter inner connector diameter L is approximately 0.26 inches.

The probe 104 can include an elongate member 302 that defines the second fluid pathway 216. The elongate member 302 can have a member length H, measured from the inlet 218 to the outlet 220. In the embodiment of FIGS. 5-7, the member length H is approximately 3.937 inches. The elongate member 302 can further have a first member diameter F-1 located proximate to the inlet 218 of the second fluid pathway 216. In the embodiment of FIGS. 5-7, the first member diameter F-1 is approximately 0.118 inches and a proximal wall thickness F-3 is approximately 0.081 inches. A second member diameter F-2 is located proximate to the outlet 220 of the second fluid pathway 216. In the embodiment of FIGS. 5-7, the second member diameter F-2 is approximately 0.057 inches and a distal wall thickness F-4 is approximately 0.02 inches. To accommodate the longer probe length, member length H, the wall thickness of the probe 104 tapers going from the proximal wall thickness F-3 and the distal wall thickness F-4. The second fluid pathway 216 can have a second fluid pathway diameter G. In the embodiment of FIGS. 5-7, the second fluid pathway diameter G is approximately 0.037 inches. Thus, in the embodiment of FIGS. 5-7, the ratio of the member length H to the second fluid pathway diameter G is approximately 106.4; the ratio of the member length H to the proximal wall thickness F-3 is approximately 4.81; the ratio of the member length H to the distal wall thickness F-4 is approximately 19.5; the ratio of the member length H to the first member diameter F-1 is approximately 33.4; the ratio of the member length H to the second member diameter F-2 is approximately 69.1; the ratio of the first member diameter F-1 to the second fluid pathway diameter G is approximately 3.2; and the ratio of the second member diameter F-2 to the second fluid pathway diameter G is approximately 1.5.

The connection portion 212 can be defined by a length R and an outer diameter S. The outer diameter S includes a plurality of helical threads. The length R of the connection portion 212 is approximately equal to the proximal length H of the connector 214, and the outer diameter S of the connection portion 212 is approximately equal to the proximal inner diameter I of the connector 214. Thus, when the connector 214 is mated with the connection portion 212, the exterior surface of the connection portion 112, defined by the length R and the outer diameter S of the connection portion 212, is in physical contact with the interior surface of the connector 214, defined by the proximal length H and the proximal inner diameter I of the connector 213. The dimensions set forth above for A-L describe the exemplary embodiment of FIGS. 5-7. With these dimensions of A-L, the dispenser 100, operating in an ambient temperature of approximately 18° C., can dispense, for example, approximately 500 μl, at a pre-selected period between dispenses of approximately once per 9 seconds, or any period between 1 second to 9 seconds, and at a pre-determined temperature of approximately 37° C.+/−2° C.

Due to the dimensions of the dispenser 100 and the placement of the heat source 230, different portions of the dispenser 100 can be maintained at different temperatures. This is depicted in FIG. 7, which shows the first structure 102 at a first set of temperatures, and the probe 104, which is indirectly heated by the heat source 230 via the core 108, at a second set of temperatures. Specifically, in some embodiments, the core 108 proximate to the outlet 206 and/or the fluid exiting the outlet 206 can be at a first temperature and/or within a first temperature range, which first temperature and/or temperature range can be preselected, and the probe proximate to the outlet 220 and/or the fluid exiting the outlet 220 can be at a second temperature and/or within a second temperature range, which second temperature and/or temperature range can be preselected. In some embodiments, the first temperature and/or temperature range can be the same as the second temperature and/or temperature range, and in some embodiments, the first temperature and/or temperature range can be different from the second temperature and/or temperature range. In some embodiments, the first temperature range can be, for example, between approximately 35° C. and 38° C., and the second temperature range can be, for example, between 25° C. and 35° C. In some embodiments, the upper limit of the first temperature range can be no more than 15° C. higher than the lower limit of the second temperature range. As seen in FIG. 7, in some embodiments, the dispenser can be operated at ambient temperatures of approximately 18° C.

With reference now to FIG. 8, a perspective view of a front side of a third embodiment of a dispenser 800 is shown. The dispenser 800 can include one or several features configured to allow the dispensing of a desired volume of fluid at a desired period between dispenses and/or at a desired temperature. While parts of this invention describes the desired dispense volume of fluid in terms of a minimum dispense volume, the desired dispense volume of fluid can be, in the alternative, a maximum dispense volume, or any dispense volume between the minimum and the maximum dispense volume.

In the embodiments of FIGS. 8A-12, the dispenser 800 can dispense up to approximately 200 µl. In other embodiments, the dispenser 800 can dispense volumes ranging from approximately 50 µl to approximately 1,000 and/or any intermediate value. In the embodiments of FIGS. 8A-12, the dispenser 100 can hold a total fluid volume of approximately 650 µl. In other embodiments, the dispenser 100 can hold a total fluid volume ranging from approximately 500 µl to approximately 6000 µl, and/or any other intermediate value.

The dispenser 800 can dispense a minimum dispense volume, at a pre-selected period between dispenses. The pre-selected period between dispenses can vary according to, for example, a desired throughput level. For example, the dispenser 800 can dispense a minimum dispense volume at a pre-selected period between dispenses of from approximately once per 9 seconds to approximately once per 4 hours, and/or any other intermediate value. When many assays need to be processed in a short amount of time, then the dispenser 800 can be configured to dispense a minimum dispense volume approximately every 9 seconds, or any period between 1 second to 9 seconds. When running a high throughput condition, such as 400 tests per hour on the Beckman Coulter Unicel DxI 800 immunoassay system, the system's dispenser dispenses every 9 seconds. By contrast, when the assay system is idle, then the dispenser 100 can be configured to dispense a minimum dispense volume in approximately 4 hours or longer. The system can be idle for more than 4 hours, such as during non-business hours. Thus, in other embodiments, the dispenser 100 can be configured to dispense a minimum dispense volume at a pre-selected period between dispenses of more than approximately 4 hours, such as from approximately 4 hours to infinity, or any other intermediate value.

The dispenser 800 can be configured to heat and dispense the fluid at a pre-selected temperature or temperature range. If the temperature profile of an assay requires the assay reaction mixture temperature to be approximately 37° C., then the dispenser may be configured to heat and dispense the fluid at a pre-selected temperature of approximately 37° C. In the embodiment of FIGS. 8A-12, the dispenser 800 can heat and dispense the fluid at a pre-selected temperature of approximately 37° C.+/−0.5° C. Alternatively, temperature profiles of other assays may require different assay reaction mixture temperatures. Thus, in other embodiments, the dispenser 100 can dispense the fluid at approximately 20° C., approximately 30° C., approximately 35° C., approximately 37° C., approximately 37° C.+/−0.7° C., approximately 37° C.+/−2° C., approximately 40° C., approximately 50° C., and/or any other intermediate value. The pre-selected temperature or temperature range can be configured by, for example, setting a heat source set point of the heat source 900. The heat source 900 is suitable for heating the first structure to the first pre-selected temperature range and the probe to a second pre-selected temperature range by setting its set point to a temperature within the first pre-selected temperature range. The set point of heat source 900 can be set to approximately 37.5° C. to heat the first structure to a first pre-selected temperature range of approximately 36-38° C. and the probe to a second pre-selected temperature range of approximately 25-36° C.

The dispenser 800 can include a body 802, also referred to herein as a "first structure," and a probe 804. The first structure 802 can be configured to allow heating of fluid contained within the first structure 802 to a desired temperature and/or to within a desired temperature range. As such, the first structure 802 can include a first fluid pathway in which fluid can be contained. In some embodiments, this first fluid pathway can include an inlet through which fluid enters the first fluid pathway and the first structure 802, and an outlet through which fluid exits the first fluid pathway and the first structure 802.

Figure 8A:
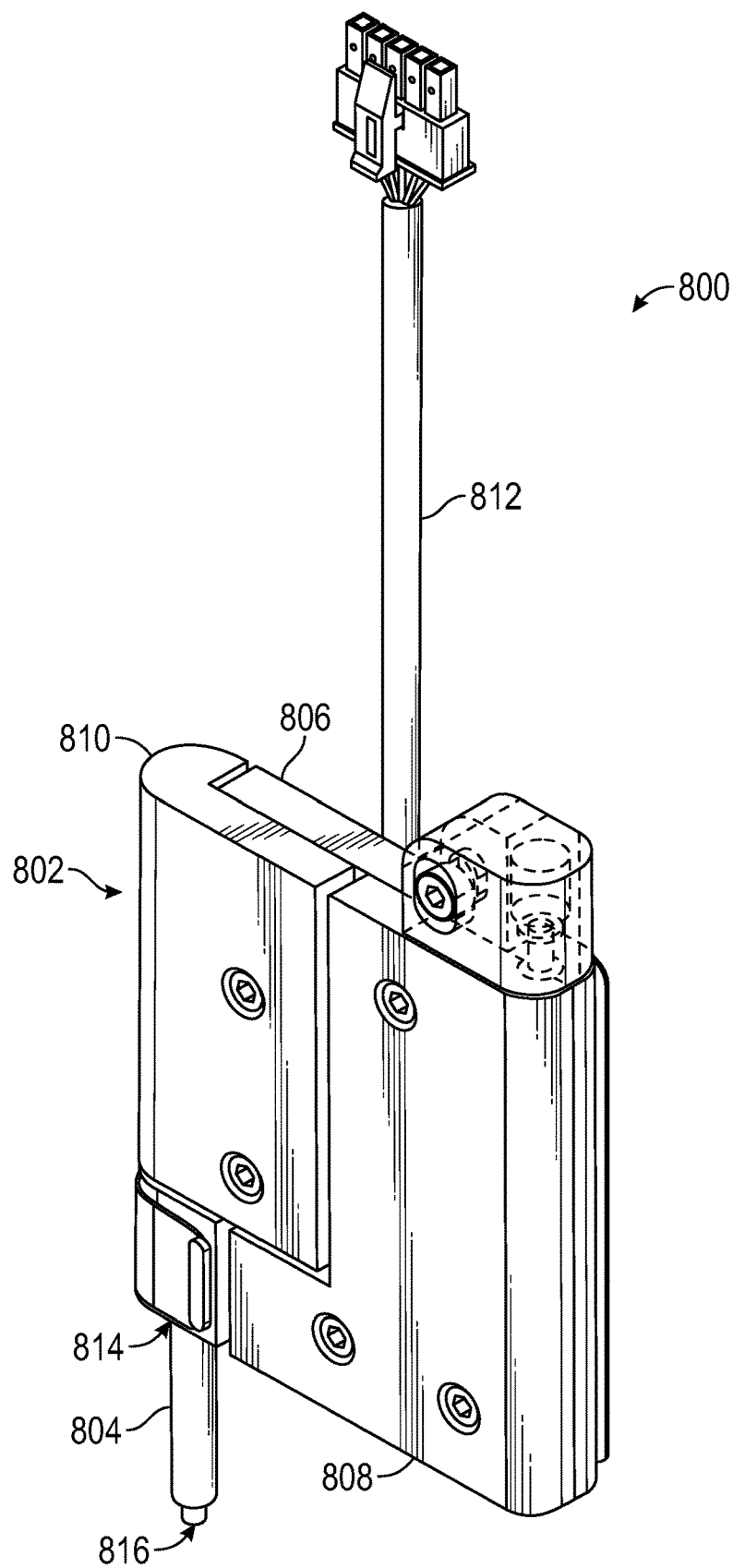
FIGS. 8A and 8B are perspective views of a front side of third embodiments of a dispenser.
Figure 8B:
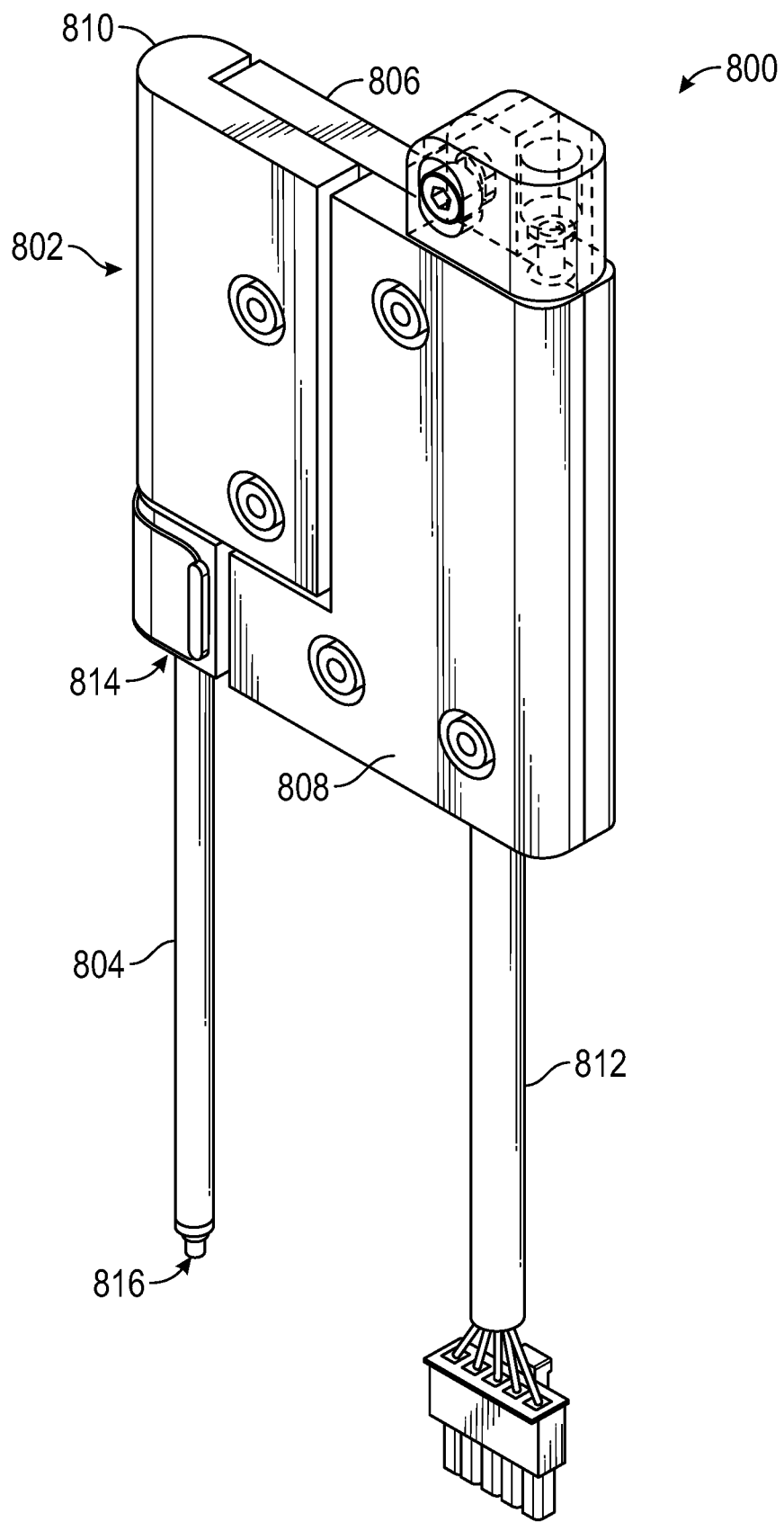

As shown in FIGS. 8A and 8B, the first structure 802 includes a back plate 806, a front plate 808, and a probe plate 810. The plates 806, 808, 810 can comprise a variety of shapes and sizes, and can be made from a variety of materials. In the embodiments of FIGS. 8A-12, the plates 806, 808, and 810 each have a thickness of approximately 0.24 inches. In other embodiments, one or several of the plates 806, 808, 810 can have a thickness of, for example, approximately 0.1 inches, approximately 0.2 inches, approximately 0.3 inches, approximately 0.4 inches, approximately 0.5 inches, approximately 0.6 inches, approximately 0.8 inches, approximately 1 inch, and/or any intermediate value.

In some embodiments, the plates 806, 808, 810 are made from aluminum, such as 6061-T6 aluminum. 6061-T6 aluminum has a thermal conductivity of approximately 167 W/mK. In other embodiments, the plates 806, 808, 810 can be made from other metal, metal alloy, or an aluminum alloy. In some embodiments, the plates 806, 808, 810 can comprise a thermal mass that can transfer heat to a fluid within a fluid channel. In some embodiments, one or several of the plates 806, 808, 810 can be made of material having a thermal conductivity of approximately 167 W/mK. In some embodiments, plates 808 and 810 can be integrated to form one plate.

The first structure 802 can further include a cable 812 that can include one or several wires that can be used to power the dispenser and/or to send/receive signals from the dispenser 800 such as, for example, one or several control signals, sensing signals, or the like.

The probe 804 can receive fluid from the first structure 802 and can deliver the fluid. The probe 804 can comprise a variety of shapes and sizes and can be made from a variety of materials that can conduct heat. The probe 804 can be in thermal communication with the heat source 900 via the back plate 806. Thus, the probe 804 can conduct heat from the back plate 806 and the heat source 900, conduct heat from the heat source 900 via the back plate 806, or a combination thereof. As will be described in FIG. 11A, in some embodiments, the probe 804 comprises a conductive core 1110 and a shell 1112. In some embodiments, the conductive core 1110 can be completely enclosed within the shell 1112, and in some embodiments, the conductive core 1110 can be partially enclosed within the shell 1112. In some embodiments, the probe 804 can have a proximal end 814 and a distal end 816, and a lumen, also referred to herein as a second fluid pathway, extending between the proximal end 814 and the distal end 816 of the probe 804. In some embodiments, the second fluid pathway of the probe 804 can hold a volume of approximately 5 μl, approximately 10 μl, approximately 20 μl, approximately 25 μl, approximately 30 μl, approximately 40 μl, approximately 50 μl, approximately 54 μl, approximately 60 μl, approximately 70 μl, approximately 75 μl, approximately 80 μl, approximately 90 μl, approximately 100 μl, approximately 150 μl, approximately 200 μl, approximately 250 μl, approximately 300 μl, and/or any other or intermediate volume.

The probe 804 is made of aluminum molded over by polypropylene. When the probe 804 is made of aluminum molded over by polypropylene, the probe 804 can exhibit a fin efficiency of approximately 0.96 and a fin effectiveness of approximately 27. A fin efficiency of approximately 0.96 means that the probe 804 can be approximately 96% as efficient as an ideal fin. A fin effectiveness of approximately 27 means that the effect of heat transfer is increased by approximately 27 times by including the probe 804 to the end of the first structure 802. Also, with the probe 804 made of aluminum molded over by polypropylene, the probe 804 can achieve a heat transfer coefficient of approximately 10 W/m$^2$K in static state.

Figure 9:
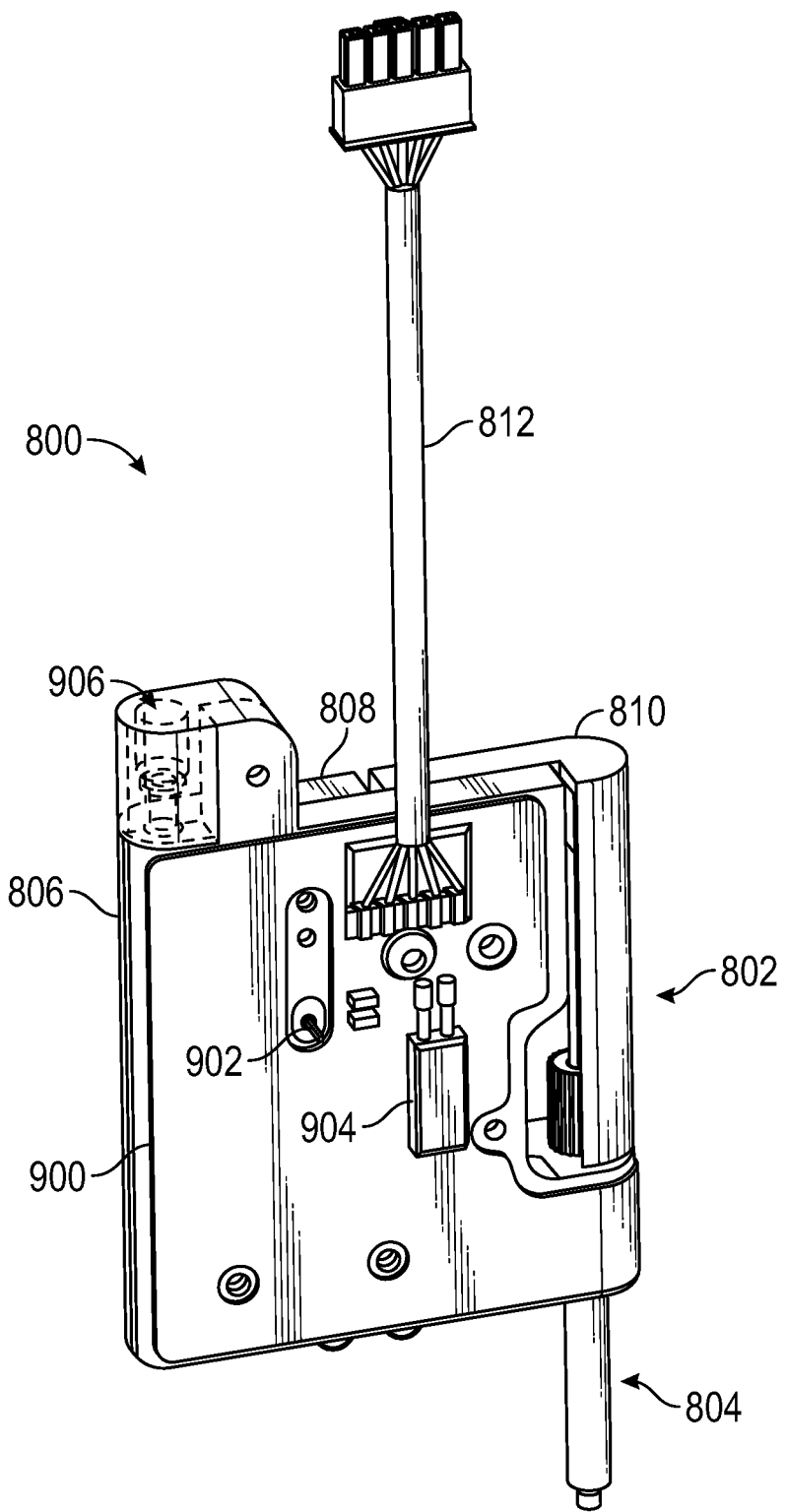
FIG. 9 is a perspective view of a back side of a third embodiment of a dispenser.

With reference now to FIG. 9, a perspective view of a back side of the dispenser 800 is shown. In this view, the first structure 802, including the plates 806, 808, 810, and the cable 812, as well as the probe 804 are visible. As further seen in this figure, the back plate 806 includes heat source 900 that can directly heat the back plate 806, indirectly heat plates 808, 810 via heat transfer from the back plate 806, and indirectly heat the probe 804 via heat transfer from the back plate 806. In embodiments, the heat source 900 can be integrated into the back plate 806, and in some embodiments, the heat source 900 can be physically and/or thermally connected with the back plate 806. In some embodiments, the heat source 900 can be directly connected to the probe 804; in some embodiments, the heat source 900 is not directly connected to the probe 804.

The heat sources 900 can comprise a variety of shapes, sizes, and types, and can be selected based on the ability of the heat source 900 to achieve the desired fluid temperature and/or fluid temperature range under a set of desired and/or expected operating conditions. In some exemplary embodiments, the heat source 900 can comprise a hydronic heat source, a resistance heat source, a heat pump, or the like. In one specific exemplary embodiment, and as shown in FIG. 9, the heat source 900 can comprise an etched foil resistance heater such as, for example, a 12 W etched foil resistance heater that can be affixed to the exterior wall of the back plate 806. In embodiments in which the heat source 900 is a resistance heat source, power for the heat source 900 can be provided via the cable 812.

The back plate 806 can include a heat sensing element such as thermistor 902. The heat sensing element can be configured to detect the temperature of all or portions of the first structure 802, and specifically of all or portions of the fluid contained in the first structure 802 and/or of the portion of the back plate 806 proximate to the heat sensing element. The heat sensing element can be electrically connected to one or several of the wires in cable 812, and can be connected to a temperature controller that can be configured to regulate the temperature of one or both of the first structure 802 and the probe 804.

The back plate 806 can further include a temperature cut-off (TCO) 904. The TCO 904 can be configured to detect a temperature of the heat source 900 and/or of one or several portions of the back plate 806 and/or of the first structure 802, and to affect the operation of the heat source 900 if the detected temperature exceeds a threshold value. In some embodiments, the TCO 904 can comprise a switch, such as, for example, a bi-metallic switch. In some embodiments, when the temperature measured by the TCO 904 exceeds a threshold value, power to the heat source 900 is decreased and/or cut.

In some embodiments, the first structure 802 can further include an inlet 906. The inlet can be configured to receive fluid into the first structure 802, and specifically into the fluid pathway of the first structure. In some embodiments, the inlet 906 shown in FIG. 9, or in any other embodiment disclosed herein, can include one or several features configured to engage with other components to allow delivery of the fluid to the inlet 906.

Figure 10:
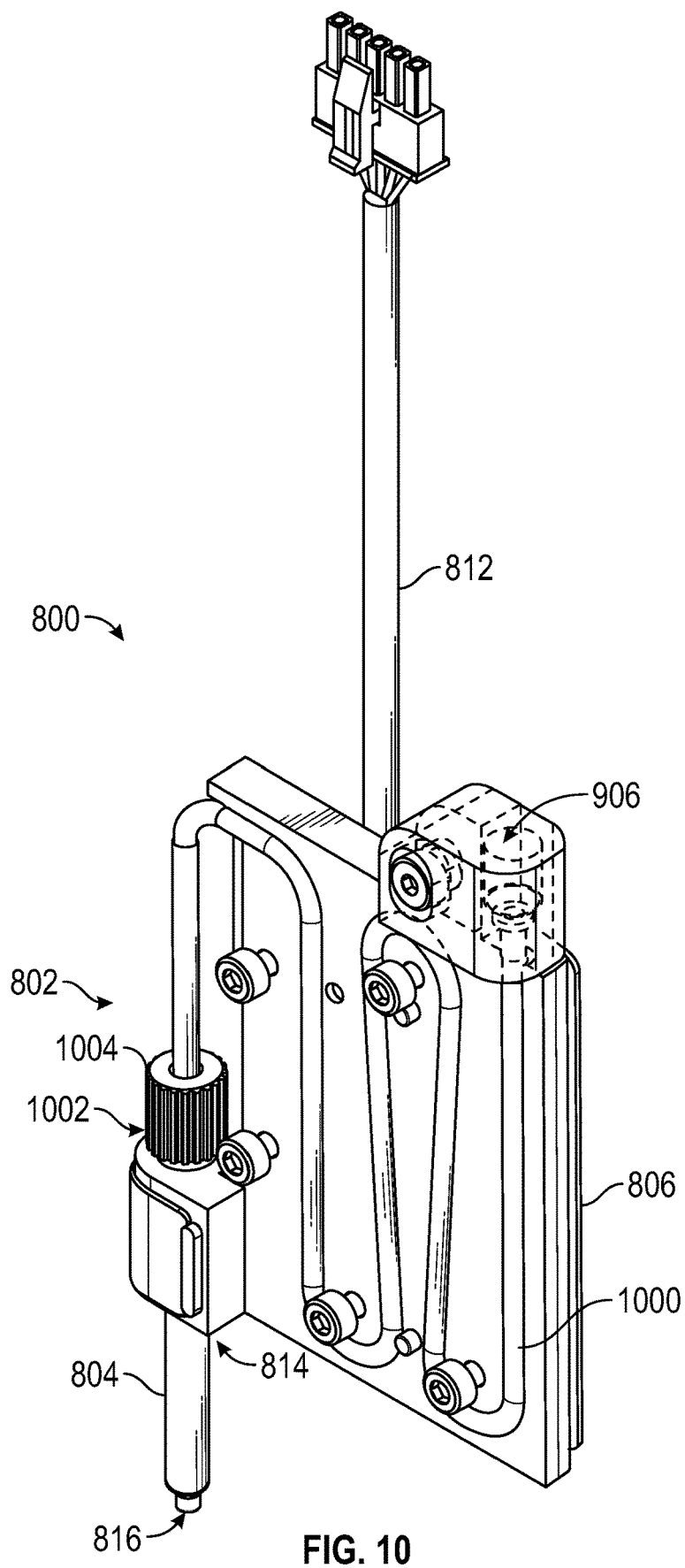
FIG. 10 is a perspective view of a third embodiment of a dispenser without a front plate and a probe plate.

With reference now to FIG. 10, a perspective view of one embodiment of the dispenser 800 without the front plate 808 and the probe plate 810 is shown. As seen in FIG. 10, a fluid tube 1000 extends from the inlet 906 to the outlet 1002. In some embodiments, the fluid tube 1000 can be located with a channel and/or groove in one or several of the plates 806, 808, 810. In the embodiments of FIGS. 8A-12, 14A and 14B, the channel and/or groove has a diameter of approximately 0.1 inches. In other embodiments, the channel and/or groove can have a diameter of, for example, approximately 0.05 inches, approximately 0.2 inches, approximately 0.3 inches, approximately 0.4 inches, approximately 0.5 inches, and/or any intermediate value.

The fluid tube 1000 can define a lumen, that can be a first fluid pathway, and that can be configured to contain fluid. As discussed above, the fluid contained in the first fluid pathway and/or second fluid pathway can be static or dynamic. The fluid tube 1000 can comprise a variety of shapes and sizes. In some embodiments, the fluid tube 1000 can be sized and shaped according to one or several design parameters such as, for example, the desired delivered fluid volume, the desired time for fluid delivery, and the desired pressure of delivered fluid. In the embodiments of FIGS. 8A-12, 14A, and 14B, the tube 100 has an outer diameter of approximately 0.1 inches, and an inner diameter of approximately 0.06 inches. In other embodiments, the tube 1000 can have an outer diameter, for example, of approximately 0.05 inches, approximately 0.2 inches, approximately 0.3 inches, approximately 0.4 inches, approximately 0.5 inches, and/or any intermediate value, and an inner diameter of, for example, approximately 0.01 inches, approximately 0.02 inches, approximately 0.03 inches, approximately 0.04 inches, approximately 0.05 inches, approximately 0.07 inches, approximately 0.08 inches, approximately 0.09 inches, approximately 0.1 inches, approximately 0.2 inches, approximately 0.3 inches, approximately 0.5 inches, approximately 0.7 inches, approximately 0.9 inches, and/or any intermediate value.

In the embodiments of FIGS. 8A-12, 14A, and 14B, the fluid tube 1000 has a length of approximately 14 inches. In other embodiments, the fluid tube 1000 can have a variety of lengths including, for example, approximately 1 inch, approximately 2 inches, approximately 3 inches, approximately 4 inches, approximately 5 inches, approximately 6 inches, approximately 7 inches, approximately 8 inches, approximately 10 inches, approximately 12 inches, approximately 16 inches, approximately 18 inches, approximately 20 inches, approximately 24 inches, and/or any intermediate value. In the embodiments of FIGS. 8A-12, 14A, and 14B, the tube 1000 can contain a volume of approximately 650 µl. In other embodiments, the tube 1000 can contain a volume of, for example, approximately 100 µl, approximately 200 µl, approximately 300 µl, approximately 400 µl, approximately 500 µl, approximately 600 µl, approximately 700 µl, approximately 800 µl, approximately 1000 µl, approximately 1500 µl, and/or any intermediate volume.

The fluid tube 1000 can be made from a variety of materials. In some embodiments, the fluid tube 1000 can be made from a material that does not react with the fluid, and in some embodiments, the fluid tube 1000 can be made from a material that reacts with the fluid. In some embodiments, the fluid tube 1000 can comprise a man-made material that does not react with the fluid, such as a heat-conductive polymer/plastic including, for example, polytetrafluoroethylene (PTFE) or polypropylene (PP). In some embodiments, the fluid tube 1000 is configured so as to not expose the fluid to light. For example, various substrate fluids, such as polyethyleneglycol (PEG), Lumi-Phos 530, or other chemiluminescent substrates, can be damaged and/or affected by exposure to light or metal, and it can be therefore desireable, to avoid such exposure. In the embodiments of FIGS. 8A-12, 14A, and 14B, the fluid tube 1000 is made from polypropylene (PP), which is not reactive with the contained fluid. Also, in the embodiments of FIGS. 8A-12, 14A, and 14B, the fluid contained in the fluid tube 1000 is not exposed to light because the fluid tube 1000 is situated within the plates 806, 808, 810.

As further seen in FIG. 10, the fluid tube 1000 can extend from the inlet 906 to the outlet 1002, where the fluid tube 1000 can fluidly connect with the proximal end 814 of the probe 804, and thereby connect the first fluid pathway of the fluid tube 1000 with the second fluid pathway of the probe 804. In some embodiments, the fluid tube 1000 can be connected to the probe 804 via one or several connectors 1004. In some embodiments, this connector 1004 can be located proximate to the probe 804, and can be, for example, a threaded connector, a snap-lock connector, or the like.

Figure 11A:
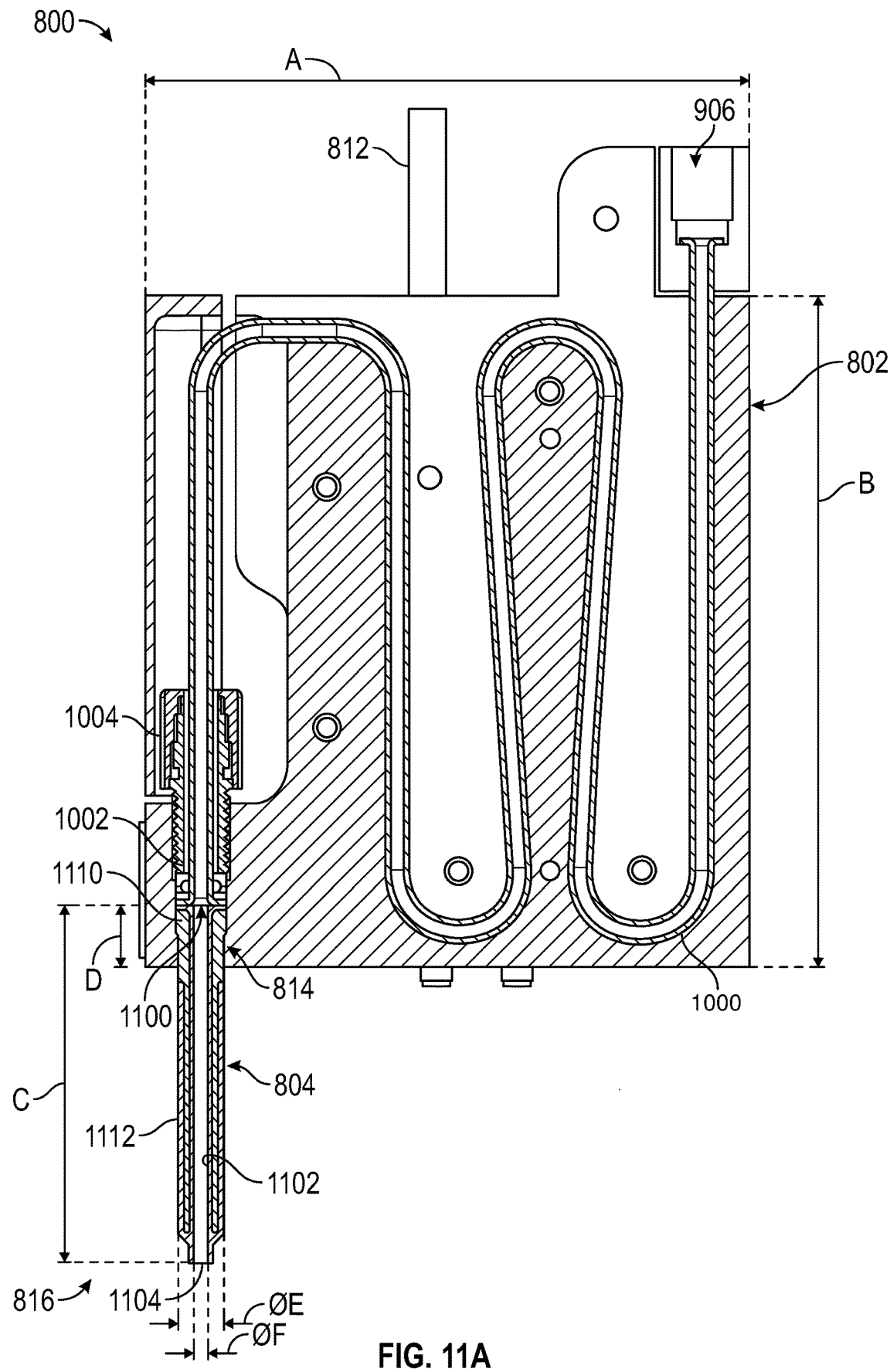
FIGS. 11A and 11B are section views of third embodiments of a dispenser.
Figure 11B:
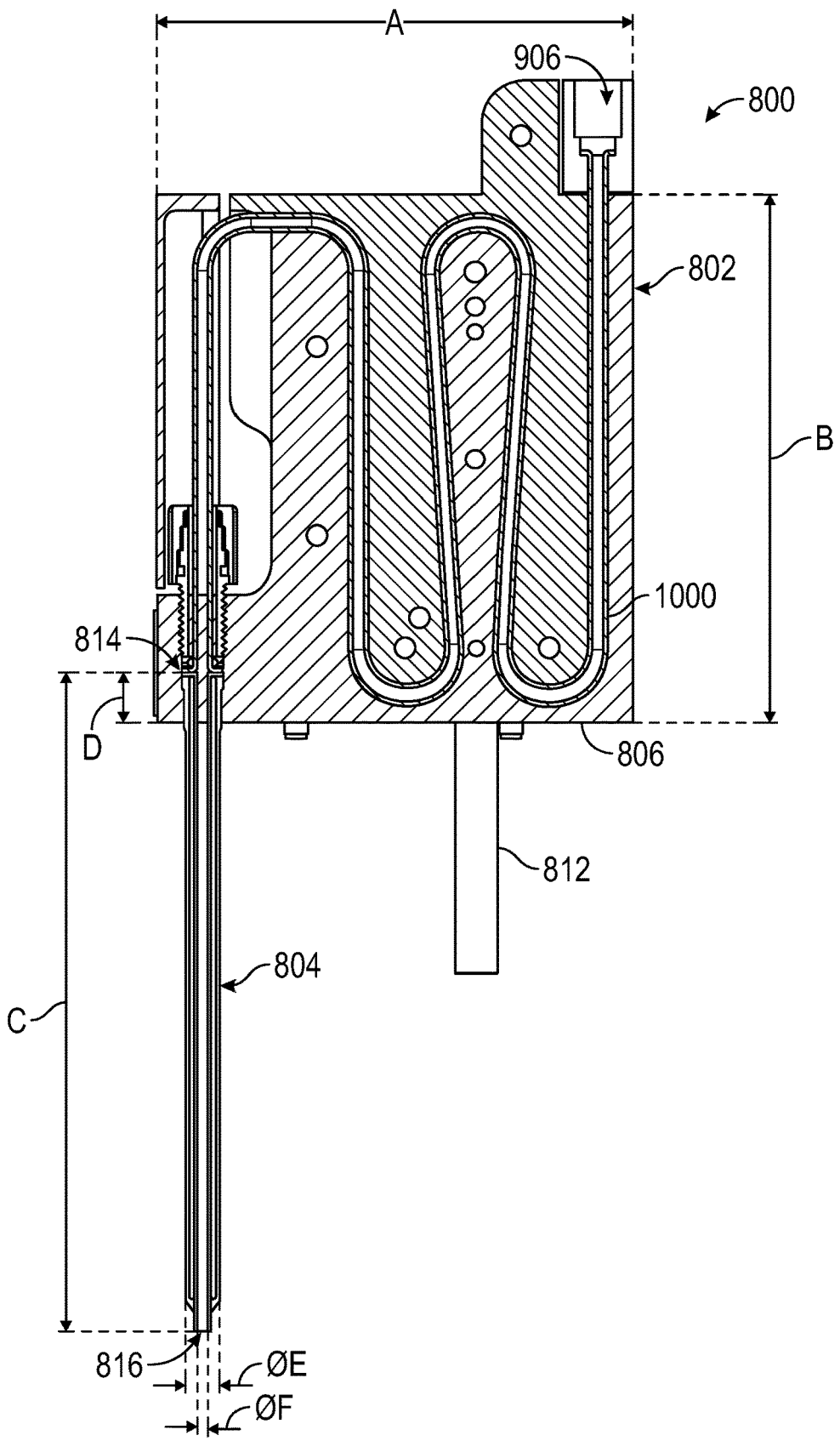

With reference now to FIGS. 11A and 11B, section views of third embodiments of the dispenser 800 are shown including, for example, the first structure 802 and the probe 804. The first structure 802 includes the back plate 806 including the inlet 906, the fluid tube 1000, the outlet 1002, and the connector 1004 connecting the fluid tube 1000 to the probe 804, and specifically fluidly connecting the outlet 1002 of the fluid tube 1000 to an inlet 1100 at the proximal end 814 of the probe 804, which inlet 1100 connects to the lumen 1102 of the probe 804 forming the second fluid pathway, and ultimately fluidly connects to the outlet 1104 of the probe 804.

As discussed above, the probe 804 of FIG. 11A comprises a conductive core 1110 and a shell 1112. In some embodiments, the conductive core 1110 can be completely enclosed within the shell 1112, and in some embodiments, the conductive core 1110 can be partially enclosed within the shell 1112. In some embodiments, the conductive core 1110 is made from aluminum and the shell 1112 is made from polypropylene (PP). Polypropylene (PP) is a heat-conductive plastic that does not react with the fluid. With the conductive core 1110 made from aluminum and the shell 1112 made from polypropylene (PP), the first fluid pathway of the first structure 800 can achieve a heat transfer coefficient, with water at approximately 18° C., of approximately 5 W/m$^2$K at static state and approximately 2,389.67 W/m$^2$K at dynamic state.

In other embodiments, the conductive core 1110 can be made from other heat conductive materials such as, aluminum alloy, nickel, nickel alloy, heat-conductive plastic, or any combination of the foregoing. In other embodiments, the shell 1112 can be made from other heat-conductive polymer/plastic such as polytetrafluoroethylene (PTFE). In some embodiments, the conductive core 1110 can comprise a material that readily conducts heat such as, for example, a metal such as nickel, a nickel alloy, aluminum, an aluminum alloy, and/or the like. In some embodiments, the conductive core 1110 of the probe 804 can comprise, for example, 6061-T6 aluminum and/or can have a thermal conductivity of approximately 167 watts per meters Kelvin (W/mK).

While the conductive core 1110 may efficiently transfer heat, in some embodiments, it may be desired to prevent the conductive core 1110 from contacting the fluid. In such an embodiment, the conductive core 1110 can be enclosed by shell 1112 so that the conductive core 1110 does not contact the fluid.

To further improve the heat transfer properties of the probe 804, in some embodiments, the conductive core 1110 can include one or several portions that are not covered and/or are thinly covered by the shell and which are thermally connected with one or more of the plates 806, 808, 810. In some embodiments, for example, portions of the conductive core 1110 at the proximal end 814 of the probe 804 are unenclosed by the shell 1112, and are in direct contact with portions of the back plate 806, thereby enabling heat transfer between the probe 804 and the back plate 806. In some embodiments, the proximal end 814 of the probe 804 has a cylindrical anchor configuration so as to anchor the probe 804 to the corresponding cylindrical anchor receiving portion of the back plate 806. To engage the probe 804 with the back plate 806, the distal end 816 is inserted and slid through the corresponding cylindrical anchor receiving portion of the back plate 806. When the proximal end 814 is anchored to the corresponding cylindrical anchor receiving portion of the back plate 806, the exterior surface of the conductive core 1110 at the proximal end 814 is in physical contact with the interior portions of the back plate 806, which enables thermal conductivity between the probe 804 and the back plate 806. Thus, when the proximal end 814 is anchored to the corresponding cylindrical anchor receiving portion of the back plate 806, the dispenser 800, operating in an ambient temperature of approximately 18° C., can dispense, for example, approximately 200 µl, at a pre-selected period between dispenses of approximately 9 seconds, or any period between 1 second to 9 seconds, and at a pre-determined temperature of approximately 37° C.+/− 0.4° C. Also, when the proximal end 814 is anchored to the corresponding cylindrical anchor receiving portion of the back plate 806, the connector 1004 can secure this connection in place. The relevant dimensions of the probe 804 and the back plate 806 are described further below with reference to FIGS. 14A and 14B.

As further seen in FIGS. 11A and 11B, the dispenser can be defined by one or several dimensions. The first structure 802 can have a length A and height B. In some embodiments of the first structure 802, length A is approximately 2.48 inches and height B is approximately 2.76 inches.

As further seen in FIGS. 11A and 11B, the probe 804 can have a probe length C as measured between the proximal and distal ends 814, 816. In some embodiments, the probe length C can be approximately 1 inch, approximately 1.48 inches, approximately 1.75 inches, approximately 2 inches, approximately 2.5 inches, approximately 3 inches, approximately 3.445 inches, approximate 4 inches, approximately 5 inches, and/or any other or intermediate value. The penetration length D is the length that the probe 804 penetrates into the first structure 802. In some embodiments, the penetration length D is approximately 0.26 inches. The probe 804 can be described by an outer probe outer diameter E and a probe inner diameter F. In some embodiments, the probe outer diameter E can be approximately 0.1 inches, approximately 0.15 inches, approximately 0.155 inches, approximately 0.189 inches, approximately 0.2 inches, and/or any other or intermediate value, and the probe inner diameter F can be approximately 0.02 inches, approximately 0.06 inches, approximately 0.039 inches, approximately 0.04 inches, approximately 0.047 inches, approximately 0.06 inches, and/or any other or intermediate value. In some embodiments, the probe 804 can hold a total fluid volume of approximately 64 µl, approximately 100 µl, approximately 150 µl, approximately 200 µl, approximately 250 µl, approximately 300 µl, and/or any other or intermediate volume. Thus, in some embodiments, the ratio of the probe length C to the probe outer diameter E can be approximately 5, approximately 6, approximately 7, approximately 7.8, approximately 9, approximately 10, approximately 15, approximately 20, approximately 22.2, approximately 25, approximately 30, and/or any other or intermediate ratio; the ratio of the probe length C to the probe inner diameter F can be approximately 20, approximately 25, approximately 30, approximately 31.4, approximately 35, approximately 40, approximately 50, approximately 70, approximately 75, approximately 80, approximately 85, approximately 88.3, approximately 90, approximately 100, approximately 150, and/or any other or intermediate ratio, and the ratio of the probe outer diameter E to the probe inner diameter F can be approximately 2, approximately 3, approximately 3.5, approximately 4, approximately 4.5, approximately 5, and/or any other or intermediate ratio.

Figure 14A:
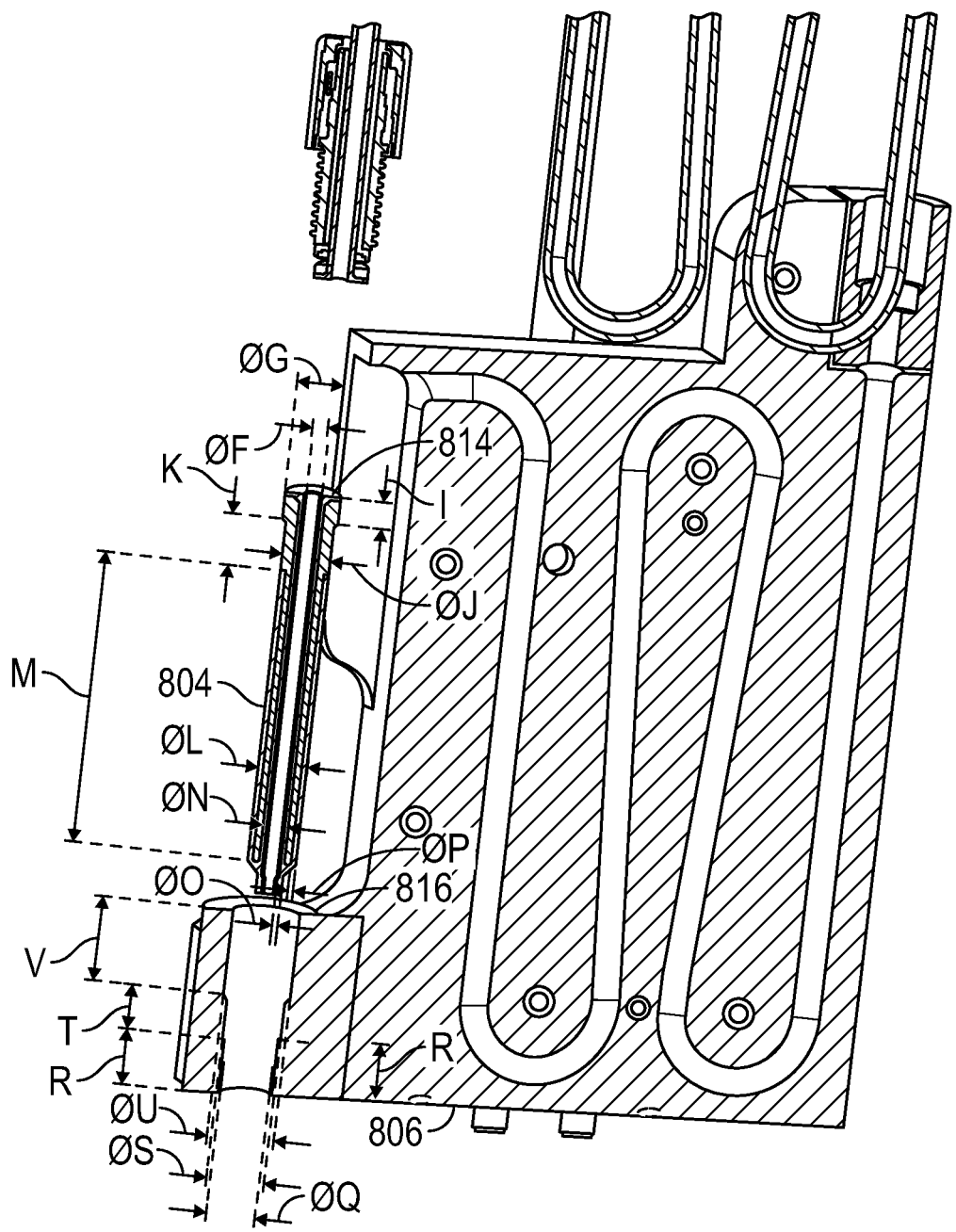
FIGS. 14A and 14B are schematic illustrations of embodiments of the temperature distribution within a heated dispenser.
Figure 14B:
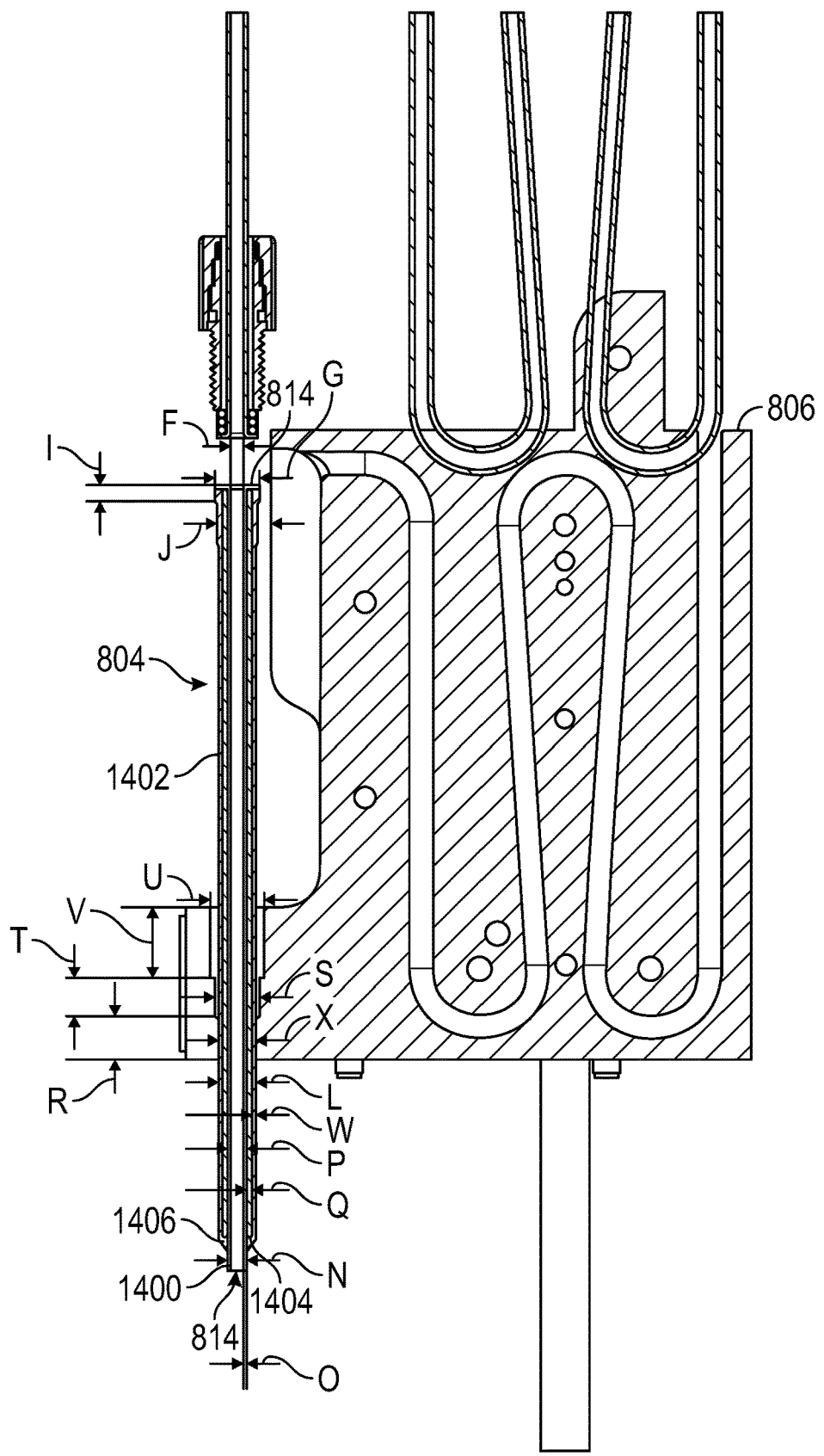

In FIGS. 14A and 14B different embodiments of the probe 804 and the back plate 806 are shown. With reference now to FIG. 14A, the metal portion of the probe 804 can be defined by a first proximal outer diameter G, a first proximal length I, a second outer diameter J, a second proximal length K, an elongated outer diameter L, an elongated length M, and a metal inner diameter N. In the embodiment of FIG. 14A, the first proximal outer diameter G is approximately 0.209 inches, the first proximal length I is approximately 0.1 inches, the second outer diameter J is approximately 0.19 inches, the second proximal length K is approximately 0.2 inches, the elongated outer diameter L is approximately 0.15 inches, the elongated length M is approximately 1.03 inches, and the metal inner diameter N is approximately 0.1 inches. An anchor of the probe 804 can be defined by the first proximal length I and the first proximal outer diameter G.

Still with reference to FIG. 14A, the non-metal heat-conductive portion of the probe 804 can be defined by the probe diameter F, an inner wall O and an outer wall P. In the embodiment of FIG. 14A, the inner wall O has a thickness of approximately 0.265 inches and the outer wall P has a thickness of approximately 0.03 inches. As shown in FIG. 14A, the non-metal heat-conductive portion is molded over the metal portion. The non-metal heat-conductive portion can conduct heat from the metal portion. As discussed, in the embodiment of FIG. 14A, the metal portion is made of aluminum and the non-metal heat-conductive portion is made of polypropylene (PP).

Still with reference to FIG. 14A, the back plate 806 can be defined by a first inner diameter Q, a first length R, a second inner diameter S, a second length T, a third inner diameter U, and a third length V. The first inner diameter Q is approximately 0.11 inches, the first length R is approximately 0.2 inches, the second inner diameter S is approximately 0.209 inches, the second length T is approximately 0.095 inches, the third inner diameter U is approximately 0.213 inches, and the third length V is approximately 0.3 inches. The corresponding cylindrical anchor receiving portion of the back plate 806 can be defined by the second inner diameter S and the second length T. The second inner diameter S of the back plate 806 is approximately equal to the first proximal outer diameter G of the probe 804, and the first inner diameter Q of the back plate 806 is approximately equal to the outer the second outer diameter J of the probe 804. Thus, when the probe 804 is anchored to the back plate 806, the first proximal length I having the first proximal outer diameter G is in physical contact with the second length T having the second inner diameter S, and the second proximal length K having the second outer diameter J is in physical contact with the first length R having the first inner diameter Q. As discussed, in the embodiment of FIG. 14A, the back plate 806 is made from aluminum. Thus, the heat transfer is from the heat source, to the aluminum back plate 806, to the aluminum portion of the probe 804, to the non-metal heat-conductive portion of the probe 804, and ultimately to the fluid contained in the probe 804.

With reference now to FIG. 14B, a second embodiment of the probe 804 is shown. The probe 804 of FIG. 14B can comprise a polymer tube 1400 extending from the proximal end 814 of the probe 804 to the distal end 816 of the probe 804. The polymer tube 1400, which can include a flange at the proximal end 814 of the probe 804, can comprise any desired polymer capable of withstanding the environment in which the polymer tube 1400 is used, and specifically can comprise any polymer capable of use with the fluids transported through the polymer tube 1400 and the temperatures of the polymer tube 1400 during use. In some embodiments, the polymer tube 1400 can comprise a fluoropolymer such as, for example, perfluoroalkoxy alkane (PFA). The polymer tube 1400 can be defined an outer diameter N, an inner diameter F, and a wall thickness O. In some embodiments, the outer diameter N of the polymer tube 1400 can be, for example, approximately, 0.05 inches, approximately 0.06 inches, approximately 0.07 inches, approximately 0.079 inches, approximately 0.08 inches, approximately 0.09 inches, approximately 0.1 inches, approximately 0.15 inches, and/or any other or intermediate value. In some embodiments, the inner diameter F can be, for example, approximately 0.01 inches, approximately 0.02 inches, approximately 0.03 inches, approximately 0.039 inches, approximately 0.04 inches, approximately 0.05 inches, approximately 0.1 inches, and/or any other or intermediate value. In some embodiments, the wall thickness O of the polymer tube 1400 can be, for example, approximately 0.005 inches, approximately 0.0075 inches, approximately 0.01 inches, approximately 0.02 inches, approximately 0.03 inches, approximately 0.04 inches, approximately 0.05 inches, and/or any other or intermediate thickness. In some embodiments, the length of the polymer tube 1400 can be equal to the length of the probe 804.

The polymer tube 1400 can be partially contained within a probe 1402 housing. The probe housing 1402 can extend from the proximal end 814 of the probe 804 towards the distal end 816 of the probe 804. In some embodiments, the probe housing 1402 can extend to the distal end 816 of the probe 804, and in some embodiments, the probe housing 1402 can terminate before reaching the distal end 816 of the probe 804. In some embodiments, the probe housing 1402 can extend along approximately 80 percent of the length of the probe 804, along approximately 85 percent of the length of the probe 804, along approximately 90 percent of the length of the probe 804, along approximately 95 percent of the length of the probe 804, and/or along any other desired or intermediate percent of the length of the probe 804.

In some embodiments, the probe housing 1402 can comprise, for example, a metallic portion 1404 that can be wholly or partially enclosed within a polymer portion 1406. In some embodiments, the metallic portion 1404 can comprise any desired metal having desired mechanical or material properties such as, for example, desired heat transfer properties. In some embodiments, the metallic portion 1404 can comprise at least one of: copper; bronze; brass; nickel; and/or aluminum. In some embodiments, the probe housing 1402 can be configured such that the metallic portion 1404 directly contacts the polymer tube 1400, and in some embodiments, the probe housing 1402 can be configured such that the metallic portion 1404 does not contact the polymer tube 1400. In some embodiments in which the metallic portion 1404 does not contact the polymer tube 1400, the metallic portion 1404 can be separated from the polymer tube 1400 by a thin layer of the polymer portion 1406, which can have a thickness of, for example, approximately 0.002 inches, approximately 0.003 inches, approximately 0.004 inches, approximately 0.005 inches, and/or any other or intermediate value.

The metallic portion 1404 can be defined by a diameter P and a wall thickness Q. In some embodiments the diameter P can be, for example, approximately 0.08 inches, approximately 0.09 inches, approximately 0.1 inches, approximately 0.12 inches, approximately 0.125 inches, approximately 0.13 inches, approximately 0.15 inches, approximately 0.2 inches, and/or any other or intermediate value. In some embodiments, the wall thickness Q can be, for example, approximately 0.005 inches, approximately 0.0075 inches, approximately 0.01 inches, approximately 0.02 inches, approximately 0.03 inches, approximately 0.04 inches, approximately 0.05 inches, and/or any other or intermediate thickness.

Similarly, the polymer portion 1406 can comprise any polymer having desired mechanical or material properties such as, for example, desired heat transfer properties, corrosion resistance, or the like. In some embodiments, the polymer portion 1406 can comprise, for example, polypropylene (PP) and/or Polyether ether ketone (PEEK). The polymer portion 1406 can be defined by an outer diameter L and a wall thickness W. In some embodiments, the outer diameter L can be, for example, approximately 0.1 inches, approximately 0.11 inches, approximately 0.12 inches, approximately 0.13 inches, approximately 0.14 inches, approximately 0.15 inches, approximately 0.155 inches, approximately 0.16 inches, approximately 0.17 inches, approximately 0.18 inches, approximately 0.19 inches, approximately 0.2 inches, and/or any other or intermediate value. In some embodiments, the wall thickness W can be, for example, approximately 0.005 inches, approximately 0.0075 inches, approximately 0.01 inches, approximately 0.015 inches, approximately 0.02 inches, approximately 0.03 inches, approximately 0.04 inches, approximately 0.05 inches, and/or any other or intermediate thickness.

The probe 804 of FIG. 14B can be further defined by a first proximal outer diameter G, a first proximal length I, and a second outer diameter J. In some embodiments, the first proximal outer diameter G is approximately 0.209 inches, the first proximal length I is approximately 0.05 inches, approximately 0.06 inches, approximately 0.065 inches, approximately 0.07 inches, approximately 0.08 inches, approximately 0.09 inches, approximately 0.1 inches, and/or any other or intermediate value. In some embodiments, the second outer diameter J is approximately 0.19 inches.

Still with reference to FIG. 14B, the back plate 806 can be defined by a first inner diameter X, a first length R, a second inner diameter S, a second length T, a third inner diameter U, and a third length V. The first inner diameter X can be approximately 0.1 inches, approximately 0.11 inches, approximately 0.12 inches, approximately 0.13 inches, approximately 0.14 inches, approximately 0.15 inches, approximately 0.16 inches, approximately 0.17 inches, approximately 0.18 inches, approximately 0.19 inches, approximately 0.2 inches, approximately 0.22 inches, and/or any other or intermediate value. The first length R can be approximately 0.15 inches, approximately 0.175 inches, approximately 0.181 inches, approximately 0.19 inches, approximately 0.2 inches, and/or any other or intermediate value. The second inner diameter S can be approximately 0.209 inches, the second length T can be approximately 0.15 inches, approximately 0.16 inches, approximately 0.17 inches, approximately 0.173 inches, approximately 0.18 inches, approximately 0.19 inches, approximately 0.2 inches, and/or any other or intermediate value. The third inner diameter U can be approximately 0.19 inches, approximately 0.2 inches, approximately 0.21 inches, approximately 0.213 inches, approximately 0.22 inches, approximately 0.23 inches, and/or any other or intermediate value. The third length V can be approximately 0.29 inches, approximately 0.3 inches, approximately 0.31 inches, approximately 0.315 inches, approximately 0.32 inches, approximately 0.33 inches, and/or any other or intermediate value. The corresponding cylindrical anchor receiving portion of the back plate 806 can be defined by the second inner diameter S and the second length T. The second inner diameter S of the back plate 806 is approximately equal to the first proximal outer diameter G of the probe 804, and the first inner diameter X of the back plate 806 is approximately equal to the outer the second outer diameter J of the probe 804. Thus, when the probe 804 is anchored to the back plate 806, the first proximal length I having the first proximal outer diameter G is in physical contact with the second length T having the second inner diameter S, and the second proximal length K having the second outer diameter J is in physical contact with the first length R having the first inner diameter X. As the back plate 806 is made from aluminum. Thus, the heat transfer is from the heat source, to the aluminum back plate 806, to the metallic portion 1404 of the probe 804, to the polymer tube 1400 of the probe 804, and ultimately to the fluid contained in the probe 804.

The dimensions set forth above describe the exemplary embodiment of FIGS. 8A-12B, and 14A-14B. With these dimensions, dispenser 800, operating in an ambient temperature of approximately 18° C., can dispense, for example, approximately 200 µl, at a pre-selected period between dispenses of approximately 9 seconds, or any period between 1 second to 9 seconds, and at a pre-determined temperature of approximately 37° C.+/−0.4° C.

Figure 12A:
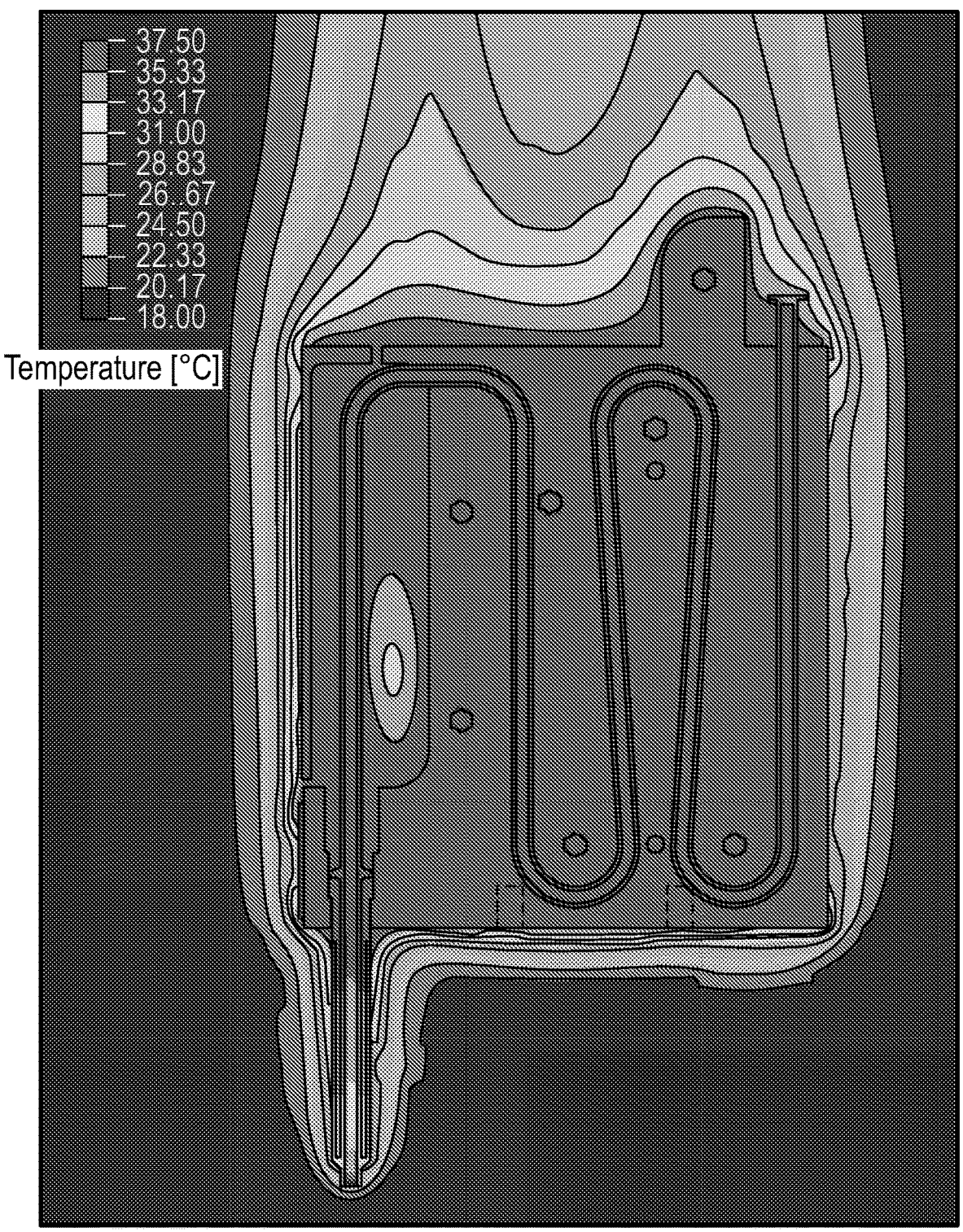
FIGS. 12A and 12B are schematic illustrations of embodiments of the temperature distribution within third embodiments of a heated dispenser.
Figure 12B:
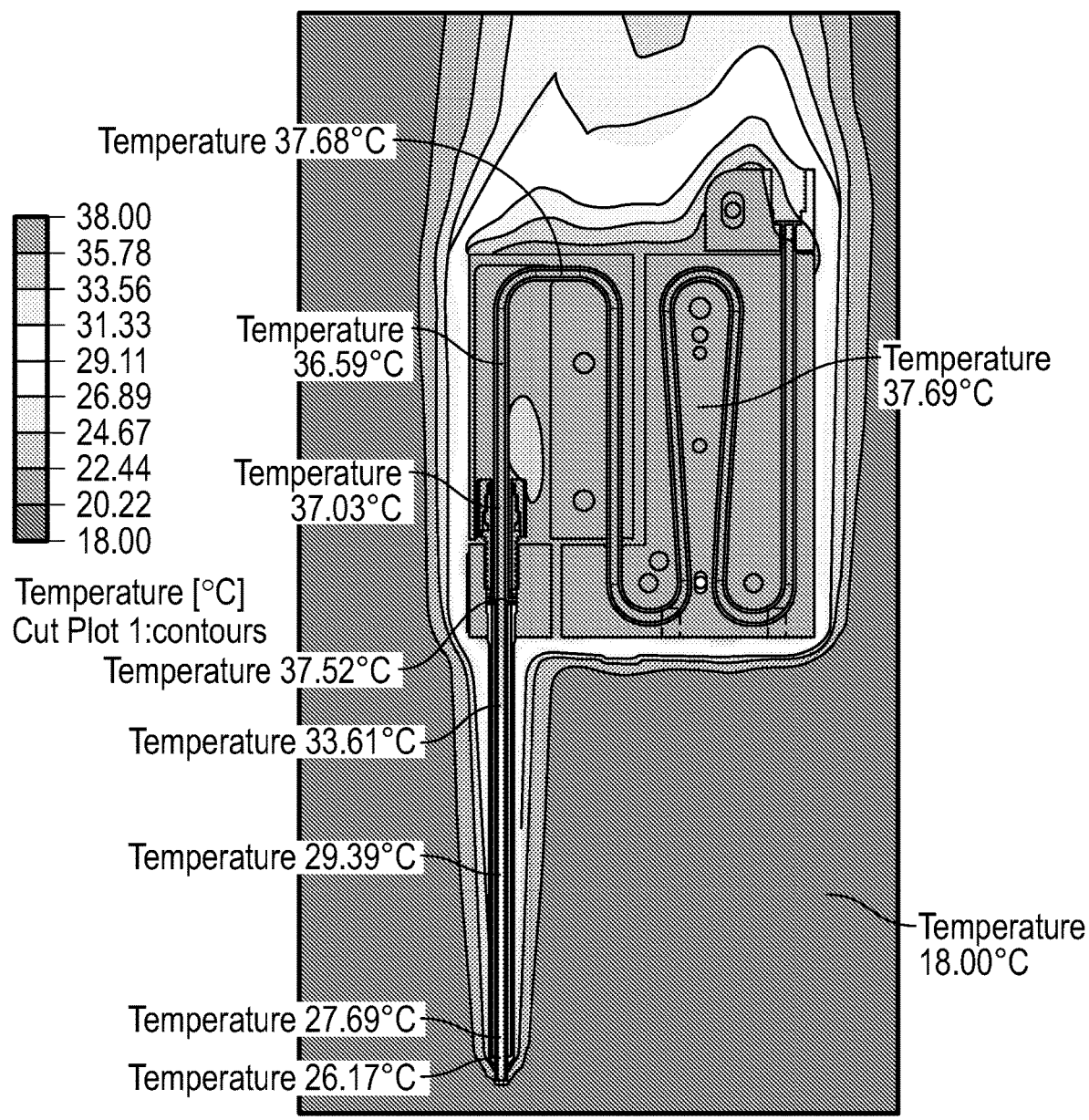

Due to the dimensions of the dispenser 800 and the placement of the heat source 900, different portions of the dispenser 800 can be maintained at different temperatures. This is depicted in FIGS. 12A and 12B, which show the first structure 802 at a first set of temperatures, and the probe 804, which is indirectly heated by the heat source 900 via the back plate 806, at a second set of temperatures. In some embodiments, the first temperature and/or temperature range can be the same as the second temperature and/or temperature range, and in some embodiments, the first temperature and/or temperature range can be different from the second temperature and/or temperature range. In some embodiments, the first temperature range can be, for example, between approximately 35° C. and 38° C., and the second temperature range can be, for example, between 25° C. and 35° C. In some embodiments, the upper limit of the first temperature range can be no more than 15° C. higher than the lower limit of the second temperature range. In some embodiments, the upper limit of the first temperature range can be no more than 7° C. higher than the lower limit of the second temperature range. As seen in FIGS. 12A and 12B, in some embodiments, the dispenser can be operated at ambient temperatures of approximately 18° C.

In some embodiments, the dispensers 100 and 800 can dispense fluid to a reaction vessel via the outlets of the probes 104 and 804, respectively. In some embodiments, the dispensers 100 and 800 are mountable onto a dispense plate assembly, such as a Beckman Coulter Access 2 Dispense Plate or a Beckman Coulter DxI Dispense Plate.

In some embodiments, a gantry may carry the dispensers 100 and/or 800. The gantry may successively move the dispenser to a reagent aspiration location, a dispense location, and a wash station. While disposed at the wash station, the dispenser may be cleaned by dispensing wash buffer through the probe outlet via the fluid pathways. This dispense action clears residual reagent from the dispenser and may also deliver heat to the dispenser through contact between the interior surface of the dispenser and the heated wash buffer. This delivery of heat by the controlled-temperature wash buffer may further control the temperature of the dispenser at the target temperature, so that the temperature of the dispenser may be maintained through the combined effects of thermal conduction from the core as described above and the intermittent transfer of heat from the wash buffer during the wash operation.

Figure 13:
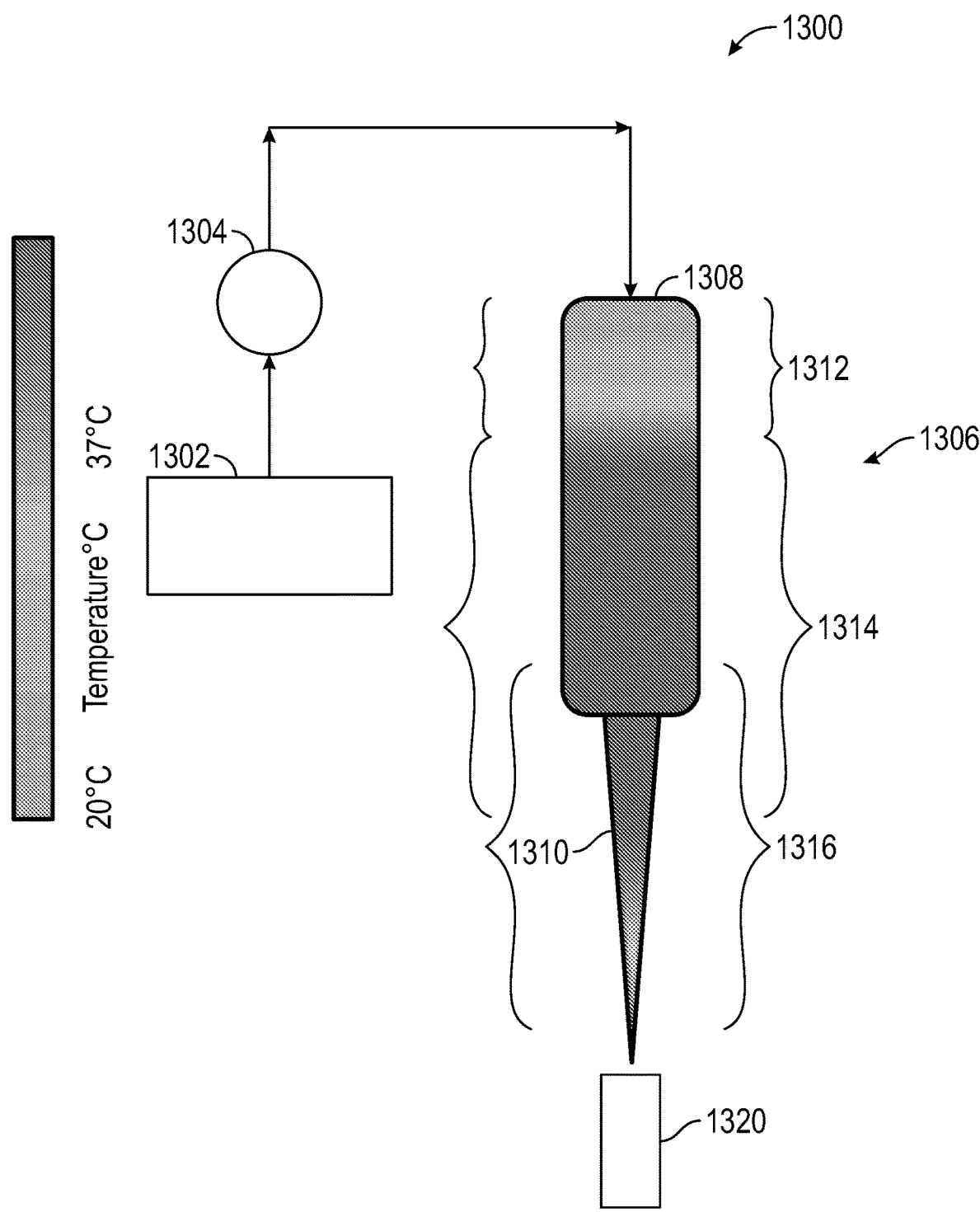
FIG. 13 is a schematic illustration of a system including a dispenser.

With reference now to FIG. 13, a schematic illustration of a system 1300 including one of the dispensers 100, 800 is shown. The system 1300 includes a fluid supply 1302 from which the fluid is removed by pump 1304. The fluid is provided to the dispenser 1306, which can be at least one of dispenser 100, 800, by the pump 1304. In some embodiments, the fluid can be provided to the first fluid pathway of the dispenser 1306. The volume of fluid provided by the pump 1304 to the dispenser 1306 can correspond to an amount of fluid to be dispensed by the dispenser 1306 such as, for example, the minimum dispense volume, the maximum dispense volume, or a dispense volume between the minimum and the maximum dispense volume. While parts of this invention describes the desired dispense volume of fluid in terms of a minimum dispense volume, the desired dispense volume of fluid can be, in the alternative, a maximum dispense volume, or any dispense volume between the minimum and the maximum dispense volume.

Different types of fluids can be stored at different temperatures. Thus, the fluid supply 1302 can be at room temperature or at chilled temperatures. With reagents, the fluid supply 1302 can store reagents at chilled temperatures. Alternatively, with wash buffers, the fluid supply 1302 can store wash buffers at room temperature. Thus, when the equipment performing the assay has to dispense reagents, wash buffers, or both, it can be beneficially able to dispense such fluids at temperatures that do not adversely affect the assay reaction mixture temperature. For example, if the temperature profile of an assay requires the assay reaction mixture temperature to be approximately 37° C., then the chilled reagents and the room temperature wash buffers may be heated up to, and dispensed at, approximately 37° C.

The dispenser 1306, which can include a first structure 1308 and a probe 1310, can be divided into different regions which correspond with the different temperatures of the dispensers 1306 and/or the different temperatures of the fluid passing through that portion of the dispenser 1306. The first structure 1308 can be at least one of first structures 102 or 802. The probe 1310 can be at least one of probes 104 or 804. These regions include a preheat zone 1312, a control zone 1314, and a dispense zone 1316. In some embodiments, the preheat zone 1312 can be configured to bring the fluid from an initial temperature to a first temperature and/or first temperature range, the control zone 1314 can be configured to maintain the temperature of the fluid at the first temperature and/or at the first temperature range, and the dispense zone 1316 can be configured to prevent the fluid from dropping below a second temperature and/or second temperature range. The dispense zone 1316 can conduct heat from the control zone 1314. In some embodiments, a portion of the dispense zone 1316 can reside in the control zone 1314.

The fluid that is contained in the first fluid pathway of the dispenser can be heated via the heat source in one or several of the zones 1312, 1314, 1316 of one or both of the first structure 1308 and the probe 1310 of the dispenser 1306. In some embodiments, during this heating process, the fluid can be heated to a first pre-selected temperature and/or temperature range, which temperature of the fluid can be determined when the fluid is at the outlet of the first structure 1308.

In some embodiments, all or portions of the received fluid can move from the first structure 1308 to the probe 1310 and can be heated to a second pre-selected temperature and/or temperature range. In some embodiments, this second temperature and/or temperature range is less than the first pre-selected temperature and/or temperature range, and in some embodiments, this heating can be achieved via energy indirectly transferred to the probe 1310 via the first structure 1308. This second temperature of the fluid can be determined at the outlet of the probe 1310.

In some embodiments, and as indicated by the gray-scale of FIG. 13, the different zones of the dispenser 1306 can be at different temperatures, and thus, the longer that fluid remains in one of the zones, the closer the temperature of the fluid will approach the temperature of the zone in which it is contained. Thus, when fluid is dispensed that has been contained for an extended period in the dispense zone 1316, the temperature of the fluid can vary from the temperature of fluid that has been contained for an extensive period of time in the control zone 1314. Thus, in some embodiments in which a single dispensing includes fluids contained for extended periods of time in multiple zones, the instantaneous temperature of the fluid dispensed during the single dispensing may vary, and may include some fluid either above or below the desired temperature and/or temperature range. However, in such embodiments, the average temperature of the dispensed fluid is at the desired temperature and/or in the desired temperature range. Thus, dispensed fluid may be at a desired temperature and/or within a desired temperature range when an instantaneous amount of dispensed fluid is at the desired temperature and/or within the desired temperature range and/or when the temperature of the combined fluid from a dispensing event is at the desired temperature and/or within the desired temperature range.

In some embodiments, the received fluid can then be dispensed by the dispenser 1306 to a reaction vessel 1320 via the outlet of the probe 1310. In some embodiments, this dispensing can occur according to a constant or varying pre-selected period between dispenses. Similarly, in some embodiments, the volume of the dispensed fluid can be a pre-selected constant or varying volume. In the equation below, the total volume of fluid, $V_T$, can be the desired dispense volume of fluid. In some embodiments, the dispensed fluid can contain fluid at the first temperature and/or temperature range and at the second temperature and/or temperature range. Due to the volumes of fluids from these temperature ranges, the combined fluid of a single dispensing can, in some embodiments, have a temperature that is at the first temperature and/or within the first temperature range. This temperature of the fluid can be determined according to the following equation, wherein:

$T_{avg}$ is the resulting average fluid temperature;
$T_h$ is the temperature of the fluid at the first temperature and/or temperature range;
$V_T$ is the total volume of fluid;
$V_i$ is the volume of fluid at the second temperature and/or temperature range; and
$T_{amb}$ is the temperature of the fluid at the second temperature and/or temperature range.

$$T_{Avg} = T_h * \frac{V_T - V_i}{V_T} + T_{amb} * \frac{V_i}{V_T}$$

Thermal resistance is a heat property and a measure of an object's resistance to heat conduction. Thermal resistance is the reciprocal of thermal conductance. The total equivalent thermal resistance of each embodiment of the dispenser can be derived using the following formula, wherein:

$R_{eq}$ is the total equivalent thermal resistance;
$T_1$ is the set temperature of the heat source;
$T_2$ is the temperature at the distal end of the probe;
Q is the wattage rating of the heat source; and
Duty is the Duty cycle of the heat source at steady state.

$$R_{eq} = \frac{T_1 - T_2}{Q * \text{Duty}}$$

For the embodiment of FIGS. 1A-4B, with the core and the probe made of Nickel 200 alloy, then a $R_{eq}$ of approximately 6.66 K/W can be achieved with a $T_1$ of approximately 37.7° C., $T_2$ of approximately 31.3° C., Q of approximately 12 W, and a Duty of approximately 8%. In some embodiments disclosed herein, the thermal resistance can be approximately from 5 K/W to 8 K/W, approximately from 6 K/W to 7 K/W, approximately from 6.25 K/W to 6.75 K/W, approximately 6.5 K/W, approximately of at least 6.5 K/W, and/or any other or intermediate value.

For the embodiment of FIGS. 5-7, with the core and the probe made of Nickel 200 alloy, then a $R_{eq}$ of approximately 11.25 K/W can be achieved with a $T_1$ of approximately 37.7° C., $T_2$ of approximately 21.5° C., Q of approximately 12 W, and a Duty of approximately 12%.

Alternatively, for the embodiment of FIGS. 5-7, with the core made of Nickel 200 alloy and the probe made of stainless steel, then a $R_{eq}$ of approximately 13.33 K/W can be achieved with a $T_1$ of approximately 37.7° C., $T_2$ of approximately 18.5° C., Q of approximately 12 W, and a Duty of approximately 12%. Compared to the embodiment of FIGS. 1-4, the embodiments of FIGS. 5-7 have a greater total equivalent thermal resistance because the length of the probe is greater.

For the embodiment of FIGS. 8A-12, 14A, and 14B, with the core made of aluminum and the probe made of polypropylene molded over aluminum, then a $R_{eq}$ of approximately 0.97 K/W can be achieved with a $T_1$ of approximately 37.5° C., $T_2$ of approximately 35.1° C., Q of approximately 12 W, and a Duty of approximately 21%. Compared to the embodiments of FIGS. 1A-7, the embodiment of FIGS. 8A-12, 14A, and 14B has a lower total equivalent thermal resistance because it is smaller in size and aluminum has a higher thermal conductivity than Nickel 200 alloy.

A method for dispensing fluid to an analyzer is also disclosed. First, a minimum dispense volume of fluid is provided to a fluid pathway of a heatable structure. The heatable structure can be at least one of first structures 102 or 802. The fluid pathway can be the first fluid pathway of at least one of first structures 102 or 802. Fluid can be provided to the fluid pathway with a pump, such as pump 1304. Fluid can be provided to the fluid pathway at its ambient temperature. Second, a heat source, which is in thermal communication with the heatable structure, heats the minimum dispense volume to a first pre-selected temperature range when the minimum dispense volume is contained at an outlet of the heatable structure. As discussed, the minimum dispense volume, contained in the fluid pathway can be fluid that is static or dynamic. The minimum dispense volume can be heated by conductive heat transfer as the minimum dispense volume draws heat energy from at least one of first structures 102 or 802. The heat source can be at least one of heat sources 230 or 900. The outlet of the heatable structure can be at least one of outlets 206 or 1002. Third, the heat source, which is also in thermal communication with a probe, heats the minimum dispense volume to a second pre-selected temperature range when the minimum dispense volume is contained in the probe. As discussed, the minimum dispense volume contained in the probe can be fluid that is static or dynamic. The probe can be at least one of probes 104 or 804. The minimum dispense volume can be heated by conductive heat transfer as the minimum dispense volume draws heat energy from at least one of probes 104 or 804. Finally, the minimum dispense volume is dispensed, at an outlet of the probe, within the first pre-selected temperature range at a pre-selected period between dispenses. The outlet of the probe can be at least one of outlets 220 or 1104.

Figure 15:
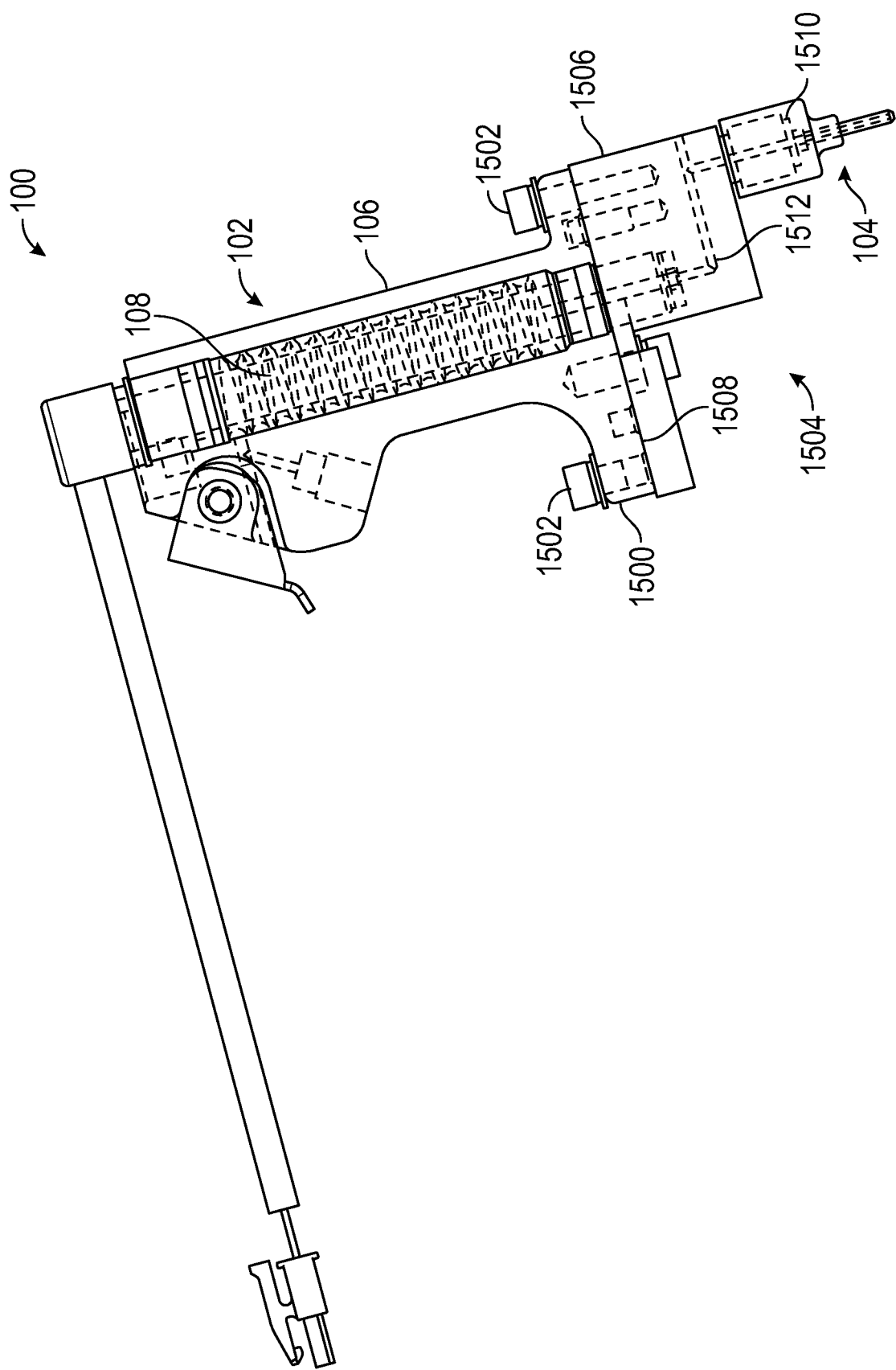
FIG. 15 is a side view of one embodiment of a dispenser with an elbow.

With reference now to FIG. 15, a side view of one embodiment of a dispenser 100 is shown. The dispenser 100 can include the heating module 102, and the probe 104. The probe 104 can include the proximal end 116, the distal end 118, and the second fluid pathway 216. The heating module 102 includes a housing 106 that includes the core 108 and a mating portion 1500 that can mate with another component of the dispenser 100. In some embodiments, the mating portion 1500 of the heating module 102 can be configured to engage with one or several connectors 1502 to connect with another component of the dispenser 100.

As seen in FIG. 15, the dispenser includes an elbow 1506 connecting the housing 106 to the probe 104. The elbow 1506 can comprise a variety of shapes and sizes and can be made from variety of materials. In some embodiments, the elbow 1506 can be made from a metal such as nickel or a nickel alloy.

The elbow 1506 can include a proximal end 1508 that can connect with the mating portion 1500 of the heating module 102, and the elbow 1506 can include a distal end 1510 that connects with the probe 104. The elbow 1506 can further include a fluid path 1512 extending from the proximal end 1508 of the elbow 1506 to the distal end 1510 of the elbow 1506. In some embodiments, the fluid path 1512 of the elbow 1506 can create a channel for fluid received from the heater module 102 to pass through the elbow 1506 and to the probe 104.

Figure 16:
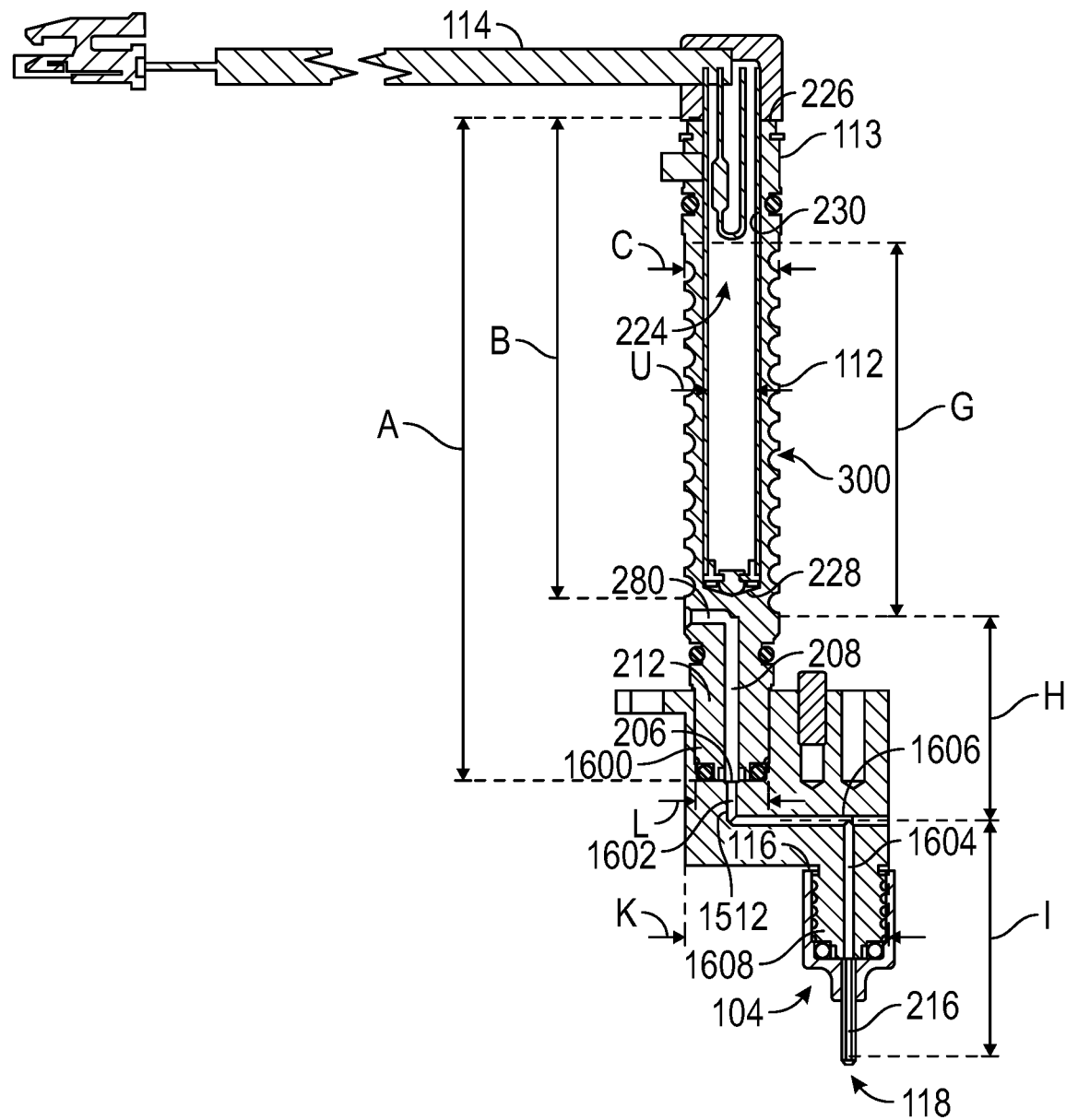
FIG. 16 is a section view of one embodiment of a dispenser with an elbow.

With reference now to FIG. 16, a section view of one embodiment of the core 108, the elbow 1506, and the probe 104 is shown. As seen, the core 108 includes the plurality of grooves 300 defined by the plurality ridges 112 located on the exterior wall 113 of the core 108. In some embodiments, the grooves 300 can have a diameter of approximately 0.01 inches, 0.02 inches, 0.03 inches, 0.04 inches, 0.047 inches, 0.05 inches, 0.06 inches, 0.07 inches, 0.08 inches, 0.09 inches, 0.1 inches, and/or any other or intermediate value.

The core 108 further includes the internal volume 224 that can have the top 226 proximate to the cable 114 and the bottom 228 proximate to the connection portion 212 of the core 108. As seen in FIG. 2, the top 226 of the internal volume 224 is open and the bottom 228 of the internal volume 224 is closed. The core 108 further includes the outlet channel 208 that extends through the connection portion 212 of the core 108 to the outlet 206, and a linking channel 280 that connects a fluidic pathway defined by at least one of the plurality of grooves 300 to the outlet channel 208. The core 108 can include a heat source 230 that can be located inside the internal volume 224 of the core 108.

As further seen in FIG. 16, the elbow 1506 includes a receiving portion 1600 sized and shaped to receive the connection portion 212 of the core. In some embodiments, both the receiving portion 1600 and the connection portion 212 can be threaded so as to allow the connection of the elbow 1506 and the core 108, and in other embodiments, one or both of the receiving portion 1600 and the connection portion 212 can be unthreaded and the elbow 1506 and the core can be connected via the mating portion 1500 of the housing 106.

The fluid pathway 1512 extending through the elbow 1506 can include an inlet path 1602, and outlet path 1604, and a connection path 1606 connecting the inlet path 1602 and the outlet path 1604. In some embodiments, the inlet path 1602 can be sized, shaped, and positioned to fluidly connect with the second fluid pathway 216 of the probe 104. The elbow 1506 can further include a probe connecting portion 1608 that can be configured to connect to the probe 104. In some embodiments, and as depicted in FIG. 16, this probe connecting portion 1608 can be threaded.

In some embodiments, the core 108 can be defined by the core length A which can be approximately 1 inch, approximately 1.5 inches, approximately 2 inches, approximately 2.5 inches, approximately 2.8 inches, approximately 2.87 inches, approximately 3 inches, approximately 3.157 inches, between 1 and 5 inches, between 2 and 4 inches, between 2.5 and 3.5 inches, between 2.75 and 3 inches, between 3 and 3.5 inches, or any other or intermediate value or within any other or intermediate range. The core 108 can be further defined by an internal volume length B measured from the top 226 to the bottom 228 of the internal volume 224. The internal volume length B of the embodiment of FIG. 16 can be approximately 1 inch, approximately 1.5 inches, approximately 2 inches, approximately 2.07 inches, approximately 2.079 inches, approximately 2.1 inches, approximately 2.5 inches, between 1 and 4 inches, between 2 and 3 inches, and/or any other or intermediate value or within any other or intermediate range. The core 108 can be further defined by a core diameter C that can be, for example, approximately 0.4 inches, approximately 0.41 inches, approximately 0.42 inches, approximately 0.43 inches, approximately 0.435 inches, approximately 0.45 inches, approximately 0.5 inches, and/or any other or intermediate value.

The core 108 can be further defined by a length G, which length G is measured from the groove closest to the top 226 of the core 108 to the linking channel 280. In some embodiments, the length G can be, for example, approximately 1.2 inches, approximately 1.3 inches, approximately 1.4 inches, approximately 1.5 inches, approximately 1.6 inches, approximately 1.625 inches, approximately 1.7 inches, approximately 1.8 inches, approximately 1.9 inches, approximately 2 inches, and/or any other or intermediate value.

In some embodiments, the dispenser 100 can be defined by length H, which length H is measured from the linking channel 280 to the connection path 1606, and by length I which is measured from the connection path 1606 to the distal end 118 of the probe 104. In some embodiments, the length H can be, for example, approximately 0.5 inches, approximately 0.6 inches, approximately 0.7 inches, approximately 0.8 inches, approximately 0.88 inches, approximately 0.9 inches, approximately 1 inch, approximately 1.5 inches, approximately 2 inches, and/or any other or intermediate value. In some embodiments, the length I can be, for example, approximately 0.7 inches, approximately 0.8 inches, approximately 0.9 inches, approximately 1 inch, approximately 1.02 inches, approximately 1.2 inches, approximately 1.2 inches, approximately 1.3 inches, approximately 1.4 inches, approximately 1.5 inches, approximately 2 inches, and/or any other or intermediate value.

As further seen in FIG. 16, the elbow 1506 can be defined by a width K, which width can be, for example, approximately 0.5 inches, approximately 0.6 inches, approximately 0.7 inches, approximately 0.8 inches, approximately 0.88 inches, approximately 0.9 inches, approximately 1 inch, approximately 1.5 inches, approximately 2 inches, and/or any other or intermediate value. Further, the receiving portion 1600 of the elbow 1506 can be defined by a diameter L. The diameter L can be, for example, approximately 0.1 inches, approximately 0.2 inches, approximately 0.3 inches, approximately 0.31 inches, approximately 0.4 inches, approximately 0.5 inches, approximately 0.7 inches, approximately 1 inch, approximately 1.5 inches, and/or any other or intermediate value.

Figure 17:
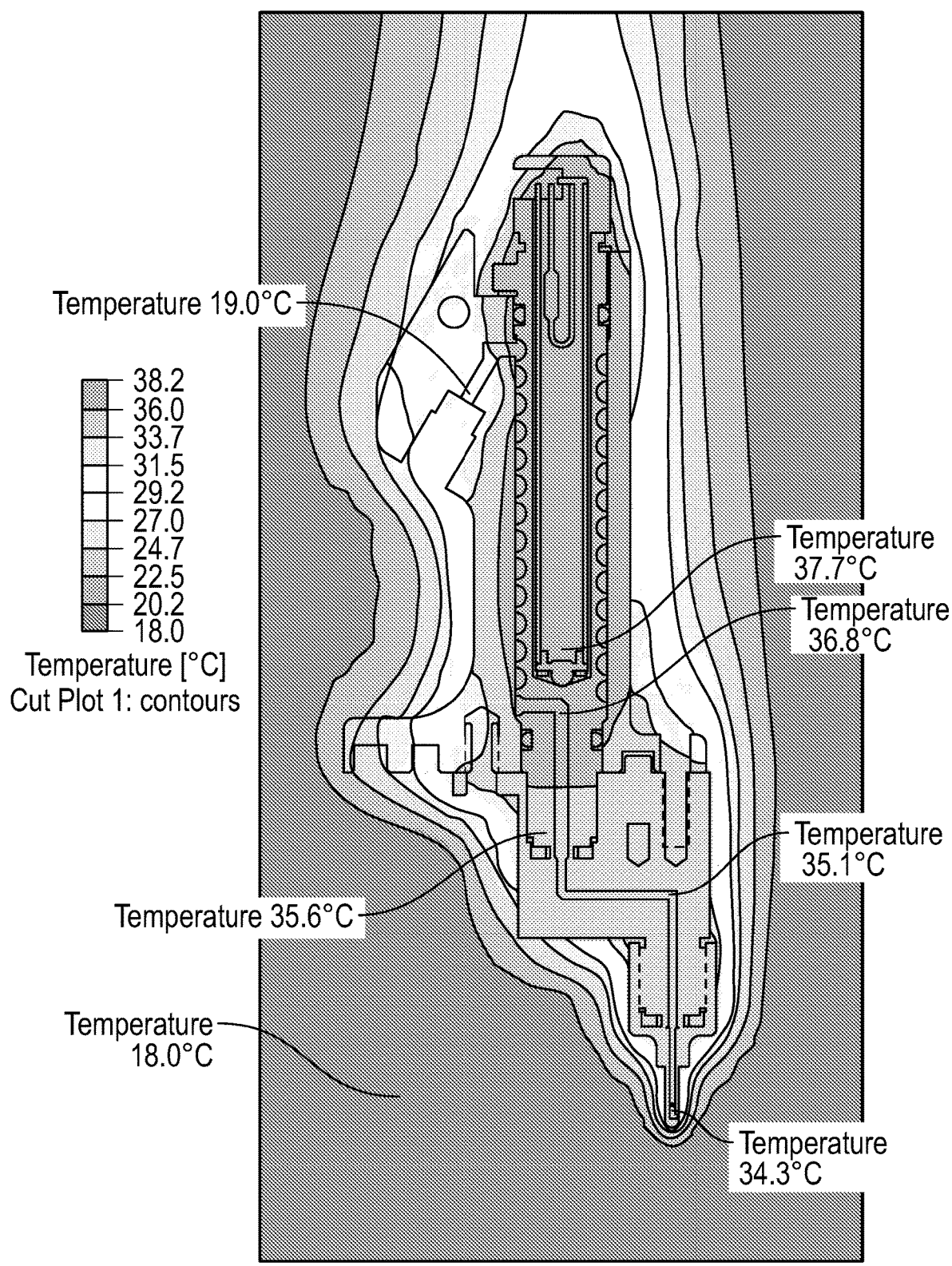
FIG. 17 is schematic illustrations of an embodiment of the temperature distribution within a dispenser including an elbow.

Due to the dimensions of the dispenser 100 and the placement of the heat source 230, different portions of the dispenser 100 can be maintained at different temperatures. This is depicted in FIG. 17, which shows the first structure 102 at a first set of temperatures, and the probe 104, which is indirectly heated by the heat source 230 via the core 108, at a second set of temperatures. Further, the elbow 1506 can be heated, via conduction from the core 108, to temperature intermediate between the temperatures of the first structure 102 and the temperatures of the probe 104. Specifically, in some embodiments, the core 108 proximate to the outlet 206 and/or the fluid exiting the outlet 206 can be at a first temperature and/or within a first temperature range, which first temperature and/or temperature range can be preselected, and the probe 104 proximate to the probe connecting portion 1608 and/or fluid exiting the probe connecting portion 1608 can be at a second temperature and/or within a second temperature range, which second temperature and/or temperature range can be preselected. In some embodiments, the first temperature and/or temperature range can be the same as the second temperature and/or temperature range, and in some embodiments, the first temperature and/or temperature range can be different from the second temperature and/or temperature range. In some embodiments, the first temperature range can be, for example, between approximately 35° C. and 38° C., and the second temperature range can be, for example, between 25° C. and 35° C. In some embodiments, the upper limit of the first temperature range can be no more than 15° C. higher than the lower limit of the second temperature range. As seen in FIG. 17, in some embodiments, the dispenser can be operated at ambient temperatures of approximately 18° C. The design of the embodiment permits operation at a range of ambient temperatures with minimal effect on the controlled temperature ranges. A dispenser for an analyzer can operate in a range of ambient temperatures, from approximately 18° C. to approximately 36° C.

In the foregoing specification, the invention is described with reference to specific embodiments thereof, but those skilled in the art will recognize that the invention is not limited thereto. Various features and aspects of the above-described invention can be used individually or jointly. Further, the invention can be utilized in any number of environments and applications beyond those described herein without departing from the broader spirit and scope of the specification. The specification and drawings are, accordingly, to be regarded as illustrative rather than restrictive. It will be recognized that the terms "comprising," "including," and "having," as used herein, are specifically intended to be read as open-ended terms of art.

What is claimed is:

1. A method of dispensing fluid in an analyzer with a dispenser, the method comprising:
   providing the dispenser with a total fluid volume, the dispenser including a heating module with a first fluid pathway and the dispenser further including a probe with a second fluid pathway, the first fluid pathway including an inlet and an outlet, the second fluid pathway including an inlet and an outlet, and the outlet of the first fluid pathway in fluid communication with the inlet of the second fluid pathway;
   providing fluid to the inlet of the first fluid pathway at an ambient temperature ($T_{amb}$);
   repeatedly dispensing a dispensed volume of fluid from the outlet of the second fluid pathway at a rate of a pre-selected period between dispenses when the dispenser is not idle; and
   transferring heat from the heating module to fluid in the first fluid pathway and to the probe and thereby repeatedly dispensing the dispensed volume of fluid from the outlet of the second fluid pathway within a pre-selected temperature range;
   containing fluid in a dispense zone and a control zone for an extended period of time when the dispenser is idle for the extended period of time, a temperature of fluid contained in the dispense zone for the extended period of time varying from a temperature of fluid contained in the control zone for the extended period of time; and
   dispensing, in a single dispensing, the fluid contained for the extended period of time from the dispense zone and the control zone;
   wherein an instantaneous temperature of at least some of the fluid contained for the extended period of time in the dispense zone and/or the control zone is either above or below the pre-selected temperature range and wherein an average temperature of the fluid in the single dispensing is within the pre-selected temperature range.

2. The method of claim 1, wherein the ambient temperature ($T_{amb}$) ranges from approximately 18 degrees Celsius to approximately 36 degrees Celsius.

3. The method of claim 1, wherein the ambient temperature ($T_{amb}$) is approximately 18 degrees Celsius.

4. The method of claim 1, wherein the pre-selected temperature range is 35 to 38 degrees Celsius.

5. The method of claim 1, wherein the pre-selected period between dispenses is approximately 8 seconds.

6. The method of claim 1, wherein the extended period of time when the dispenser is idle is approximately 7 minutes.

7. The method of claim 1, wherein the extended period of time when the dispenser is idle is more than 4 hours.

8. The method of claim 1, wherein the total fluid volume of the dispenser is approximately 1035 µl.

9. The method of claim 1, wherein the total fluid volume of the dispenser is up to 5000 µl.

10. The method of claim 1, wherein at least a portion of the first fluid pathway has a helical configuration.

11. The method of claim 1, wherein the fluid provided to the inlet of the first fluid pathway is provided with a pump.

12. The method of claim 1, wherein the fluid provided to the inlet (of the first fluid pathway is one of a wash buffer, a substrate, or a reagent.

13. The method of claim 1, wherein the probe is suitable for aspirating fluid through the outlet of the second fluid pathway.

14. The method of claim 1, wherein the dispensed volume is a volume ranging from approximately 50 µl to approximately 500 µl.

15. The method of claim 1, wherein the dispensed volume is a volume of approximately 500 µl.

16. The method of claim 1, wherein:
   repeatedly dispensing the dispensed volume of fluid from the outlet of the second fluid pathway results in a series of dispenses each having an average temperature of dispensed fluid;
   the series of dispenses are each separated by a period ranging from 8 seconds to 4 hours; and
   a range of the average temperatures of dispensed fluid is not larger than 2 degrees Celsius.

17. The method of claim 16, further comprising providing a controller, wherein a feedback loop of the controller receives an input of the ambient temperature ($T_{amb}$) and thereby controls heat energy produced by the heating module.

18. The method of claim 16, wherein between the first fluid pathway and the second fluid pathway, fluid flows only in a direction from the first fluid pathway to the second fluid pathway during the series of dispenses.

19. The method of claim 16, wherein during the series of dispenses, the range of the average temperatures of dispensed fluid is maintained without purging.

20. The method of claim 1, wherein the probe is removable from the heating module for replacement and/or service.

* * * * *